United States Patent
Horiuchi et al.

(10) Patent No.: US 7,869,728 B2
(45) Date of Patent: Jan. 11, 2011

(54) DENSITY DETECTION DEVICE AND IMAGE FORMING APPARATUS

(75) Inventors: Nobuhiro Horiuchi, Nara (JP); Tomoyuki Oda, Kyoto (JP)

(73) Assignee: Kyocera Mita Corporation (JP)

( * ) Notice: Subject to any disclaimer, the term of this patent is extended or adjusted under 35 U.S.C. 154(b) by 71 days.

(21) Appl. No.: 12/469,445

(22) Filed: May 20, 2009

(65) Prior Publication Data

US 2009/0297193 A1 Dec. 3, 2009

(30) Foreign Application Priority Data

| May 29, 2008 | (JP) | ............................ 2008-141188 |
| May 29, 2008 | (JP) | ............................ 2008-141189 |
| May 29, 2008 | (JP) | ............................ 2008-141190 |

(51) Int. Cl.
  *G03G 15/10* (2006.01)
(52) U.S. Cl. ........................................ 399/57; 73/32 R
(58) Field of Classification Search ................ 399/38, 399/55, 57, 120, 237; 73/32 R
  See application file for complete search history.

(56) References Cited

U.S. PATENT DOCUMENTS

| 6,819,888 B2* | 11/2004 | Teraoka et al. ................. 399/57 |
| 6,945,631 B2* | 9/2005 | Adachi ......................... 347/55 |
| 6,957,586 B2* | 10/2005 | Sprague .................... 73/861.22 |

FOREIGN PATENT DOCUMENTS

JP   2005-315948 A   11/2005

\* cited by examiner

*Primary Examiner*—Hoan Tran
(74) *Attorney, Agent, or Firm*—Ostrolenk Faber LLP

(57) ABSTRACT

In a density detection device, a casing includes an internal space. An inflow path is communicated with the internal space through an inlet facing the internal space. An outflow path is communicated with the internal space through an outlet facing the internal space. A base is provided in the internal space to block the liquid flowing from the inlet. The base has a top side positioned above the inlet. A movable member has a bottom side opposed to the top side of the base. The movable member is configured to move to cause the bottom side to be close to and away from the top side of the base. A density detection section is configured to detect density of a liquid layer formed between the bottom side and the top side while the bottom side is positioned close to the top side at predetermined distance.

16 Claims, 15 Drawing Sheets

DENSITY DETECTION DEVICE AND IMAGE FORMING APPARATUS

CROSS-REFERENCE TO RELATED APPLICATIONS

This application claims priority under 35 U.S.C. §119 to Japanese Patent Application Nos. 2008-141188, 2008-141189, and 2008-141190, all of which were filed on May 29, 2008. The entire disclosure of Japanese Patent Application Nos. 2008-141188, 2008-141189, and 2008-141190 are hereby incorporated herein by reference.

BACKGROUND OF THE INVENTION

1. Field of the Invention

The present invention relates to a density detection device and an image forming apparatus including the same.

2. Background Art

A density detection device is a device for detecting density of solute or dispersoid in liquid. A conventional density device has been configured to irradiate a liquid layer in a narrow gap formed in a liquid container with a light and to detect the density of the liquid based on a decay ratio of the light transmitting through the liquid layer.

According to the conventional density detection device, however, flow of the liquid around the narrow gap may affect formation of the liquid layer. For example, pressure of the liquid around the narrow slit may prevent the liquid layer from being formed in the desired thickness. Additionally, every time the liquid layer is formed, its thickness may vary. In such a case, it is difficult to detect accurately the liquid density.

Furthermore, according to the conventional density detection device, it is necessary to move accurately a moving unit to a predetermined position for enhancing accuracy of the density detection. However, thickness of the liquid layer will be unstable when the moving unit tilts against the wall of the liquid container or when the tilt angle of the moving unit against the wall varies every time the density detection is executed. Consequently, accuracy of the density detection will be lowered.

Also, according to the conventional density detection device, the top of the liquid container is opened. Liquid in the liquid container may leak out of the liquid container when the moving unit is moved.

SUMMARY OF THE INVENTION

Accordingly, aspects of the present invention have been created to solve the above-mentioned problems occurring in the conventional practice, and to provide a density detection device for enhancing accuracy in detecting liquid density and an image forming apparatus including the same. Also, aspects of the present invention have been created to provide a density detection device to enhance accuracy of detecting liquid density and simultaneously to prevent liquid from leaking out of a liquid container and an image forming apparatus including the same.

A density detection device according to an aspect of the present invention includes a casing, an inflow path, an outflow path, a base, a movable member, and a density detection section. The casing includes an internal space to cause liquid to pass. The inflow path causes the liquid to pass. The inflow path is communicated with the internal space through an inlet. The inlet faces the internal space. The outflow path causes the liquid to pass. The outflow path is communicated with the internal space through an outlet. The outlet faces the internal space. The base is provided in the internal space to block the liquid flowing from the inlet. The base has a top side positioned above the inlet. The movable member has a bottom side opposed to the top side of the base. The movable member is configured to move to cause the bottom side to be close to and away from the top side of the base. The density detection section is configured to detect density of a liquid layer formed between the bottom side of the movable member and the top side of the base while the bottom side of the movable member is closely positioned to the top side of the base at predetermined distance.

A density detection device according to another aspect of the present invention includes a casing, a first liquid layer formation surface, a movable member, a retainer, a spacer, and a density detection section. The casing includes an internal space to receive inflow of liquid. The first liquid layer formation surface is provided in the internal space. The movable member includes a second liquid layer formation surface opposed to the first liquid layer formation surface. Furthermore, the movable member is configured to move to cause the second liquid layer formation surface to be close to and away from the first liquid layer formation surface. The retainer retains the movable member while the movable member is configured to move freely. The spacer keeps distance between the first and second liquid layer formation surfaces to predetermined distance by making contact with the first and second liquid layer formation surfaces. The density detection section is configured to detect density of a liquid layer formed between the first and second liquid layer formation surfaces while the second liquid layer formation surface is positioned closed to the first liquid layer formation surface.

A density detection device according to yet another aspect of the present invention includes a casing, a first liquid layer formation surface, a movable member, a density detection section, and a sealing member. The casing includes an internal space and an opening. The internal space receives inflow of liquid. The opening is formed above the internal space, and is communicated with the internal space. The first liquid layer formation surface is provided in the internal space. The movable member includes a second liquid layer formation surface opposed to the first liquid layer formation surface above the first liquid layer formation surface. The movable member is configured to move to cause the second liquid layer formation surface to be close to and away from the first liquid layer formation surface. The density detection section is configured to detect density of a liquid layer formed between the first and second liquid layer formation surfaces while the second liquid layer formation surface is positioned close to the first liquid layer formation surface at a predetermined distance. The sealing member includes a through-hole to receive insertion of the movable member. The through-hole has a brim to restrict horizontal movement of the movable member. The sealing member seals the opening of the casing with the movable member.

DETAILED DESCRIPTION OF THE EMBODIMENTS

An image forming apparatus according to a preferred embodiment of the present invention will be hereinafter explained in detail with reference to the drawings. The drawings emphatically illustrate an apparatus and its elements with their positions and dimensions not necessarily drawn to scale for easy understanding. Therefore, positions and sizes of the apparatus and its elements can differ from their actual sizes, dimensions, and positions. Additionally, the following embodiment describes a printer as an example of an image forming apparatus of the present invention. However, the image forming apparatus of the present invention is not necessarily limited to it. For example, the image forming apparatus of the present invention may be a copier or a so-called multifunction peripheral (MFP) with functions of a copier and a facsimile machine. It should be also noted that after-mentioned specific configurations of the elements and others may be suitably changed and/or modified.

1. Configuration 1-1. Entire Configuration

Figure 1:
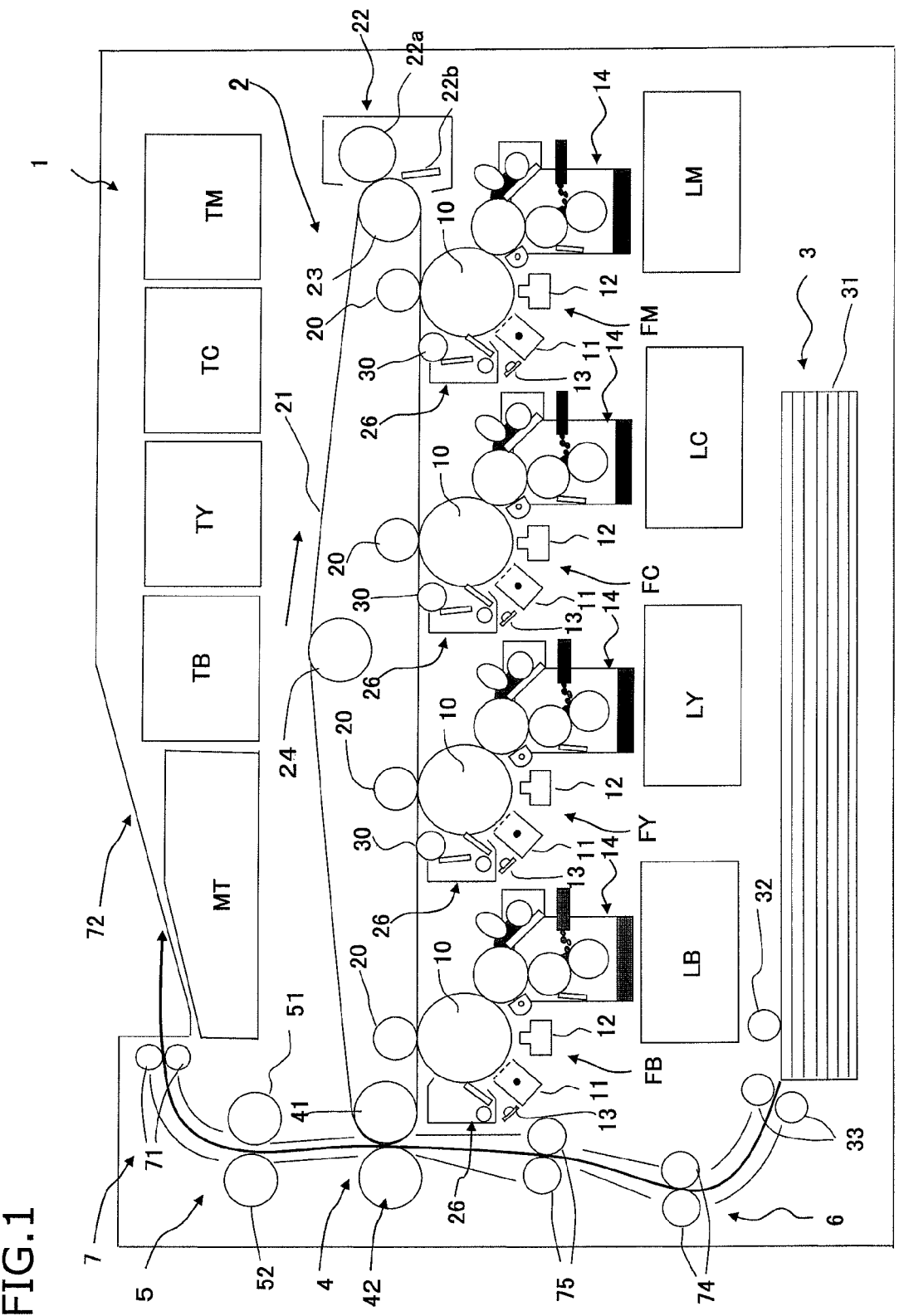
FIG. 1 is a schematic cross-sectional view of an entire color printer according to a preferred embodiment of the present invention.

FIG. 1 illustrates a color printer 1 as an image forming apparatus according to a preferred embodiment of the present invention. The color printer 1 includes an image forming section 2, a paper storage section 3, a secondary transfer section 4, a fixation section 5, a paper transportation section 6, and a discharge section 7. The image forming section 2 is a tandem type image former, and is configured to form a toner image based on image data. The paper storage section 3 is configured to store a single or plurality of sheets of paper (i.e., an example of recording media). The secondary transfer section 4 is configured to transfer the toner image formed in the image forming section 2 onto a sheet of paper. The fixation section 5 is configured to fix the toner image transferred on the sheet of paper to the sheet of paper. The paper transportation section 6 is configured to transport the sheet of paper from the paper storage section 3 to the discharge section 7.

The discharge section 7 is configured to discharge the sheet of paper to which the toner image is fixed.

The image forming section 2 includes an intermediate transfer belt 21, a cleaning unit 22, and a plurality of image formation units FB, FY, FC, and FM.

The intermediate transfer belt 21 is a conductive endless (i.e., loop-shaped) member having preferably conductivity. As illustrated in arrows of FIGS. 1 and 2, the intermediate transfer belt 21 is configured to be circularly driven in the clockwise direction. The width of the intermediate transfer belt 21 is preferably greater than that of a sheet of paper with the greatest width usable in the color printer 1. Note the term "width" means length in a perpendicular direction to a paper transportation direction. Additionally, the outside surface of the intermediate transfer belt 21 is hereinafter referred to as the "front surface" whereas its inner surface is referred to as the "back surface." Furthermore, the intermediate transfer belt 21 is wrapped around a driving roller 41, a driven roller 23 and a tension roller 24. When the driving roller 41 rotates by means of driving force transmitted from a driving motor (not illustrated in the figure), the intermediate transfer belt 21 is accordingly driven. Then, the driven roller 23 and the tension roller 24 drives in conjunction with circulation of the intermediate transfer belt 21. In this case, the tension roller 24 is configured to apply appropriate tension to the intermediate transfer belt 21 to prevent the intermediate transfer belt 21 from being loosened.

The cleaning unit 22 is configured to clean the intermediate transfer belt 21. The cleaning unit 22 includes a cleaning roller 22a and a cleaning blade 22b.

The image formation units FB, FY, FC, and FM are aligned in the vicinity of the intermediate transfer belt 21. More specifically, they are arranged between the cleaning unit 22 and the secondary transfer section 4. The image formation units FB, FY, FC, and FM respectively correspond to liquid developers of four colors: black (Bk); yellow (Y); cyan (C); and magenta (M). Note the image formation units may not be necessarily arranged in the order as illustrated in FIG. 1. However, this order is preferable in consideration of impact of the combination of colors on a finally obtained image.

Additionally, each of the image formation units (FB/FY/FC/FM) is provided with a liquid developer circulation device (LB/LY/LC/LM), a toner tank (TB/TY/TC/TM) and a main carrier tank MT. With this structure, the image formation units FB, FY, FC and FM are configured to supply and to recover liquid developers of four colors, respectively. Details of the liquid developer circulation devices LB, LY, LC, and LM will be hereinafter explained.

Figure 2:
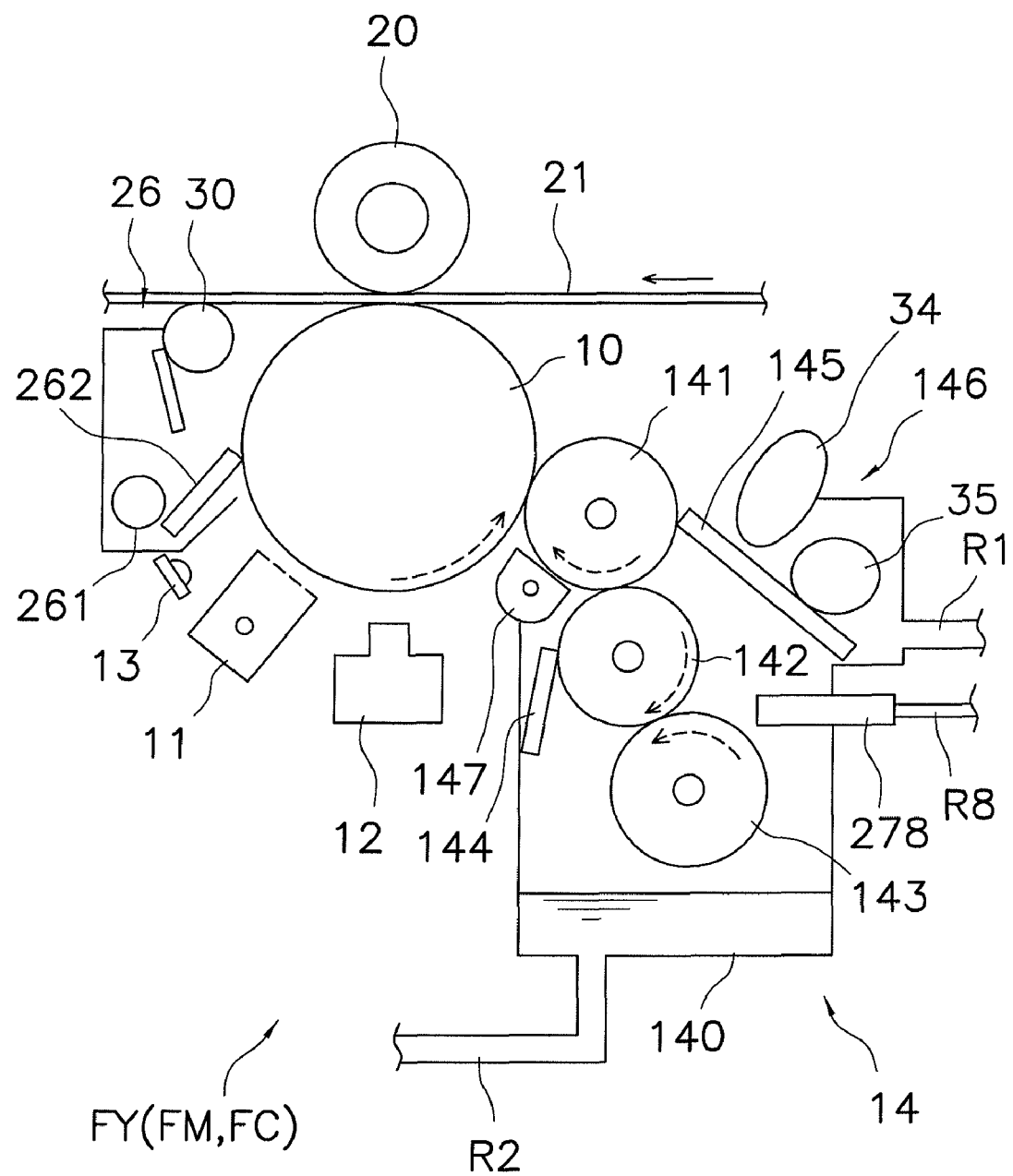
FIG. 2 is an enlarged cross-sectional view of an image forming unit of the color printer.

As illustrated in FIG. 2, each of the image formation units FY, FC, and FM is provided with a photosensitive drum 10, an electrostatic charge device 11, an exposure device 12, a development device 14, a primary transfer roller 20, a cleaning device 26, a neutralization device 13, and a liquid carrier removal roller 30. On the other hand, the image formation unit FB is arranged closest to the secondary transfer section 4 in the four image formation units FB, FY, FC, and FM. The image formation unit FB is basically the same as the other image formation units FY, FC, and FM. However, the image formation unit FB is different from the other formation units in that it is not provided with the liquid carrier removal roller 30.

The photosensitive drum 10 is a columnar member. The photosensitive drum 10 is configured to carry a charged toner image on its surface. Note the toner is positively charged in the present embodiment. As illustrated in a dashed arrow of FIG. 2, the photosensitive drum 10 is a member configured to rotate in the counter-clockwise direction.

The electrostatic charge device 11 is configured to charge uniformly the surface of the photosensitive drum 10 with a predetermined polarity and potential.

The exposure device 12 includes a light source such as a light emission diode (LED). The exposure device 12 is configured to irradiate the surface of the uniformly charged photosensitive drum 10 with a light in accordance with image data to be inputted from an external machine. Accordingly, charges of the exposed portion are removed, and an electrostatic latent image is formed on the surface of the photosensitive drum 10.

The development device 14 is configured to hold oppositely developer including toner and liquid carrier to the electrostatic latent image on the surface of the photosensitive drum 10. Accordingly, the toner attaches to the electrostatic latent image. In other words, the electrostatic latent image is developed as a toner image.

The development device 14 includes a development container 140, a development roller 141, a supply roller 142, a support roller 143, a supply roller blade 144, a development cleaning blade 145, a developer recovery device 146, and a development roller electrostatic charger 147.

The development container 140 receives a supply of the liquid developer including the toner and the liquid carrier. As explained below, the liquid developer is supplied from a supply nozzle 278 into the development container 140 after the ratio of the toner with respect to the liquid carrier is preliminarily regulated. Note the liquid developer is supplied toward a part of the support roller 143 in the vicinity of a nip portion formed by the supply roller 142 and the support roller 143. Excessive supplied liquid developer drops below the support roller 143, and is stored at the bottom of the development container 140. The stored liquid developer is recovered by the liquid developer circulation device through a flow path R2.

The support roller 143 is positioned in approximately the center of the development container 140. Additionally, the support roller 143 makes contact with the supply roller 142 from below. Thus the support roller 143 and the supply roller 142 form the nip portion. The supply roller 142 is arranged obliquely above the support roller 143. In other words, the supply roller 142 is off from a position located immediately above the support roller 143 to the direction away from the supply nozzle 278. A groove is formed on the surface of the supply roller 142 to hold the liquid developer. As illustrated with dashed arrows in FIG. 2, the support roller 143 is configured to rotate in the counter-clockwise direction whereas the supply roller 142 is configured to rotate in the clockwise direction.

The liquid developer supplied from the supply nozzle 278 is temporarily held on the rotation-directionally upstream side of the nip portion formed by the supply roller 142 and the support roller 143. Subsequently, the held liquid developer is carried to the above in conjunction with the rotation of the supply roller 142 and the support 143 while being held in the groove of the supply roller 142. The supply roller blade 144 makes contact with and presses the surface of the supply roller 142 to regulate the amount of the liquid developer held by the supply roller 142 to predetermined amount. Excessiveness of the liquid developer is scraped by the supply roller blade 144, and is stored at the bottom of the development container 140. The stored liquid developer is recovered by the liquid developer circulation device through the flow path R2.

The development roller 141 is arranged at an opening formed on the top of the development container 140. The development roller 141 makes contact with the supply roller 142. The development roller 141 is configured to rotate in the same direction as the supply roller 142. Accordingly, at the nip portion where the development roller 141 makes contact with the support roller 142, the surface of the development roller 141 moves in the opposite direction to the supply roller 142. With the configuration, the liquid developer held on the surface of the supply roller 142 is received by the surface of the development roller 141. In this case, thickness of the liquid developer layer on the supply roller 142 is regulated to a predetermined thickness. Therefore, the thickness of the liquid developer layer on the surface of the development roller 141 is accordingly maintained at a predetermined thickness.

The development roller electrostatic charger 147 is configured to impress an electric field with the same polarity as the charged polarity of toner to move the toner in the liquid developer layer carried by the development roller 141 to the surface of the development roller 141. Accordingly, development efficiency will be enhanced. The development roller electrostatic charger 147 is opposed to the development roller 141. Furthermore, the developer roller electrostatic charger 147 is positioned in the rotation-directionally downstream side of the development roller 141 seen from a contact portion between the development roller 141 and the supply roller 142. The development roller electrostatic charger 147 is also positioned in the rotation-directionally upstream side of the development roller 141 seen from a contact portion between the development roller 141 and the photosensitive drum 10.

The development roller 141 makes contact with the photosensitive drum 10. Furthermore, the potential of the development bias to be applied to the development roller 141 is different from that of the area of the electrostatic latent image on the surface of the photosensitive drum 10 (i.e., the area where charges are removed by the exposure device 12). Accordingly, the toner on the development roller 141 attaches to the surface of the photosensitive drum 10 by way of the potential difference. The toner image is thus formed on the surface of the photosensitive drum 10 in accordance with the image data.

The development cleaning blade 145 makes contact with the surface of the development roller 141. Furthermore, the contact part of the development cleaning blade 145 and the development roller 141 is positioned in the rotation-directionally downstream side of the development roller 141 seen from the contact portion between the development roller 141 and the photosensitive drum 10. Simultaneously, the contact part is positioned in the rotation-directionally upstream side of the development roller 141 seen from the contact portion between the development roller 141 and the supply roller 142. The development cleaning blade 145 is configured to remove the liquid developer remaining on the surface of the development roller 141 after a development operation with respect to the photosensitive drum 10.

The developer recovery device 146 is configured to recover the liquid developer removed by the development cleaning blade 145 and sends the recovered liquid developer to a flow path R1 of the liquid developer circulation device. The liquid developer flows down the surface of the development cleaning blade 145. However, viscosity of the liquid developer is high. Therefore, the developer recovery device 146 is provided with auxiliary rollers 34 and 35 to support movement of the liquid developer to the flow path R1.

The primary transfer roller 20 is arranged on the back surface of the intermediate transfer belt 21. The primary transfer roller 20 is opposed to the photosensitive drum 10. The primary transfer roller 20 is configured to receive voltage from a power source (not illustrated in the figure) in the primary transfer operation. In this case, the voltage applied to the primary transfer roller 20 has the opposite polarity to the toner in the toner image (i.e., negative polarity in the present embodiment). In other words, the primary transfer roller 20 is configured to apply voltage of the opposite polarity to the toner to the intermediate transfer belt 21 in a position that the primary transfer roller 20 makes contact with the intermediate transfer belt 21. The intermediate transfer belt 21 is a conductive member. Therefore, the toner is attracted to the front surface of the intermediate transfer belt 21 by the applied voltage.

The cleaning device 26 is configured to remove the liquid developer remaining on the photosensitive drum 10 without being transferred to the intermediate transfer belt 21. The cleaning device 26 includes a cleaning blade 262 and a transportation screw 261.

The cleaning blade 262 is a plate-shaped member extending in the direction of the rotation axis of the photosensitive drum 10. The cleaning blade 262 is configured to scrape the liquid developer remaining on the surface of the photosensitive drum 10. The edge of the cleaning blade 262 slides along and makes contact with the surface of the photosensitive drum 10. Thus the cleaning blade 262 scrapes the liquid developer remaining on the photosensitive drum 10 in conjunction with rotation of the photosensitive drum 10.

The transportation screw 261 is arranged in the interior of the cleaning device 26. The transportation screw 261 is configured to transport the liquid developer stored in the cleaning device 26 after being scraped by the cleaning blade 262 to a first recovery container 279 (to be described below) outside the cleaning device 26. Furthermore, the transportation screw 261 is configured to transport the liquid carrier stored in the cleaning device 26 after being removed from the intermediate transfer belt 21 by the liquid carrier removal roller 30 (to be described below) to the first recovery container 279.

The neutralization device 13 includes a light source to neutralize electric charges. The neutralization device 13 is configured to neutralize electric charges on the surface of the photosensitive drum 10 by the irradiation of the light source. For the next image formation, the neutralization device 13 is configured to neutralize electric charges after the cleaning blade 262 removes the liquid developer from the surface of the photosensitive drum 10.

The liquid carrier removal roller 30 is an approximately columnar-shaped member. The liquid carrier removal roller 30 is configured to rotate around a rotational axis in parallel to that of the photosensitive drum 10. The liquid carrier removal roller 30 is configured to rotate in the same direction as the photosensitive drum 10. The liquid carrier removal roller 30 is arranged closer to the secondary transfer section 4 than to the contact portion between the photosensitive drum 10 and the intermediate transfer belt 21. The liquid carrier removal roller 30 is a member to remove the liquid carrier from the front surface of the intermediate transfer belt 21. After being removed by the liquid carrier removal roller 30, the liquid carrier is stored in the cleaning device 26.

The paper storage section 3 in FIG. 1 is configured to store a single or plurality of sheets of paper. The paper storage section 3 is arranged in the lower part of the color printer 1. The paper storage section 3 includes a paper feeding cassette 31 to store a single or plurality of sheets of paper, a paper feeding roller 32 and a pair of paper separation rollers 33.

The secondary transfer section 4 is configured to transfer the toner image formed on the intermediate transfer belt 21 to a sheet of paper. The secondary transfer section 4 and the aforementioned primary transfer roller 20 make up a transfer device. The secondary transfer section 4 includes the driving roller 41 to drive the intermediate transfer belt 21 and a secondary transfer roller 42. The secondary transfer roller 42 is pressed toward the driving roller 41 while the intermediate transfer belt 21 is interposed between them.

The fixation section 5 is configured to fix the toner image onto a sheet of paper. The fixation section 5 is arranged above the secondary transfer section 4. The fixation section 5 includes a heat roller 51 and a pressure roller 52. The pressure roller 52 is opposed to the heat roller 51, and is configured to press the heat roller 51.

The paper transportation section 6 includes a plurality of pairs of transportation rollers 74 and a pair of resist rollers 75. The paper transportation section 6 is configured to transport a sheet of paper from the paper storage section 3 to the secondary transfer section 4, the fixation section 5, and the discharge section 7 with the rollers. FIG. 1 illustrates only a pair of transportation rollers 74 and omits illustration of the other pairs of transportation rollers.

The discharge section 7 is configured to discharge a sheet of paper after the fixation section 5 fixes the toner image onto the sheet of paper. The discharge section 7 includes a plurality of pairs of discharge rollers 71 and a discharge tray 72 provided on the top of the color printer 1. FIG. 1 illustrates only a pair of discharge rollers 71 and omits illustration of the other pairs of discharge rollers.

1-2 Configuration of Liquid Developer Circulation Devices LB, LY, LC and LM

Figure 3:
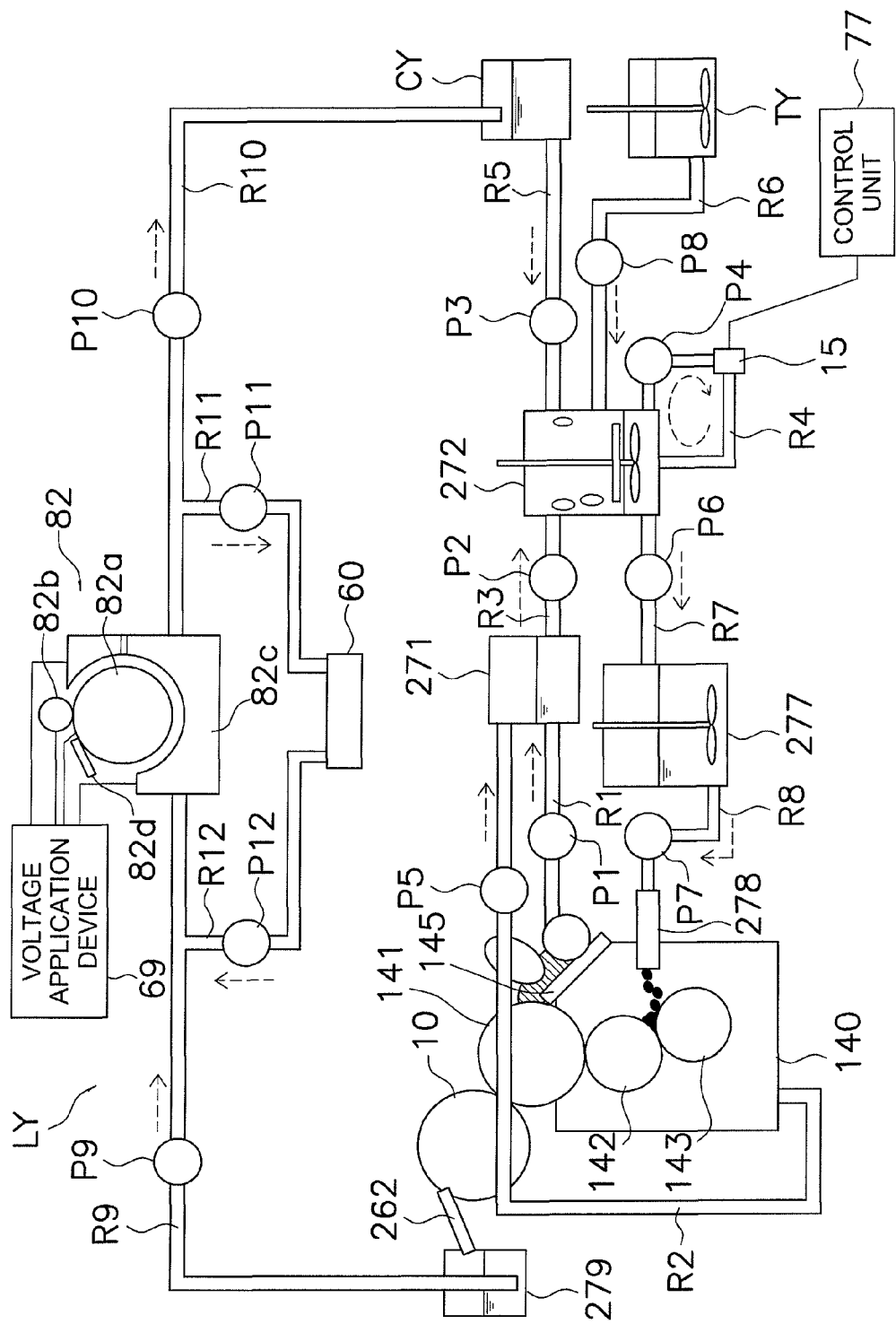
FIG. 3 is a schematic cross-sectional view of an entire liquid developer circulation device of the color printer.

FIG. 3 is a view of a schematic diagram of the entire liquid developer circulation device LY. The liquid developer circulation device LY is configured to circulate and to reuse the liquid developer. Structures of the liquid developer circulation devices LY, LB, LC, and LM are basically the same. Therefore, only a structure of the liquid developer circulation device LY will be hereinafter explained. For example, the liquid developer to be circulated by the liquid developer circulation device LY includes developer (i.e., mixture of the toner and the liquid carrier) scraped from the surface of the development roller 141 by the development cleaning blade 145, developer not having been supplied to the development roller 141 from the supply roller 142, excessive developer remaining after being supplied to the support roller 143 from the supply nozzle 278 and developer scraped from the photosensitive drum 10 by the cleaning device 26.

The liquid developer circulation device LY includes a second recovery container 271, a regulation container 272, a first density detection device 15, the carrier tank CY, the toner tank TY, a reserve tank 277, the supply nozzle 278, the first recovery container 279, a separation-extraction device 82, a second density detection device 60, and a plurality of pumps P1 to P12.

The second recovery container 271 is connected to the development device 14 through the flow path R1. The pump P1 is attached to a predetermined part of the flow path R1. The pump P1 is configured to move the liquid developer scraped from the surface of the development roller 141 to the second recovery container 271. Furthermore, the second recovery container 271 is connected to the bottom of the development container 140 through the flow path R2. The pump P5 is attached to a predetermined part of the flow path R2. The pump P5 is configured to send the liquid developer from the development container 140 to the second recovery container 271. In short, the second recovery container 271 is a tank to store the developer recovered from the development device 14.

The regulation container 272 is connected to the second recovery container 271. The regulation container 272 is configured to prepare developer to be supplied to the development device 14. Specifically, the regulation container 272 is configured to regulate toner density in the developer. The regulation container 272 is connected to the second recovery container 271 through a flow path R3 and a pump P2 is attached to the flow path R3. The pump P2 is configured to send the liquid developer from the second recovery container 271 to the regulation container 272.

The first density detection device 15 is configured to detect toner density in the liquid developer stored in the regulation container 272. The first density detection device 15 is connected to a loop flow path R4. Both ends of the loop flow path R4 are connected to the regulation container 272. Furthermore, a pump P4 is attached to the loop flow path R4. Specifically, the pump P4 is disposed upstream of the first density detection device 15. The pump P4 is configured to circulate the liquid developer in the loop flow path R4. The first density detection device 15 will be hereinafter explained in detail.

The carrier tank CY stores the liquid carrier. The liquid carrier is used to reduce toner density (hereinafter simply referred to as "density") in the liquid developer stored in the regulation container 272. The carrier tank CY is connected to the regulation container 272 through a flow path R5. Furthermore, a pump P3 is attached to the flow path R5. The pump P3 is configured to send the liquid carrier from the carrier tank CY to the regulation container 272. The carrier tank CY is configured to receive a supply of the liquid carrier from the main carrier tank MT (see FIG. 1) shared by four colors. The carrier tank CY and the main carrier tank MT are connected through a branch pipe (not illustrated in the figure). Furthermore, a pump (not illustrated in the figure) is attached to the branch pipe. When the amount of the liquid carrier in the carrier tank CY becomes less than a predetermined amount, the pump is configured to send the liquid carrier of predetermined amount from the main carrier tank MT to the carrier tank CY.

The toner tank TY stores the liquid developer of higher density than the liquid developer to be used in the development device 14. The liquid developer is used to increase density of the developer stored in the regulation container 272. The toner tank TY is connected to the regulation container 272 through a flow path R6. Furthermore, a pump P8 is attached to the flow path R6. The pump P8 is configured to send the liquid developer from the toner tank TY to the regulation container 272.

The reserve tank 277 is configured to store the liquid developer to be supplied to the development device 14. The reserve tank 277 is connected to the regulation container 272 through a flow path R7. Furthermore, a pump P6 is attached to the flow path R7. The pump P6 is configured to send the liquid developer from the regulation container 272 to the reserve tank 277. Also, the reserve tank 277 is connected to the supply nozzle 278 through a flow path R8. Furthermore, a pump P7 is attached to the flow path R8. The pump P7 is configured to send the liquid developer from the reserve tank 277 to the supply nozzle 278.

The supply nozzle 278 is configured to supply the liquid developer to the development device 14.

The first recovery container 279 is configured to store temporarily the liquid developer removed from the photosensitive drum 10 by the cleaning device 26. Furthermore, the first recovery container 279 is configured to store temporarily the liquid carrier removed from the intermediate transfer belt 21 by the liquid carrier removal roller 30.

The separation-extraction device 82 is configured to separate the liquid developer into the toner and the liquid carrier, and separately to extract the toner and the liquid carrier. The separation-extraction device 82 is connected to the first recovery container 279 through a flow path R9. Furthermore, a pump P9 is attached to the flow path R9. The pump P9 is configured to send the liquid developer stored in the first recovery container 279 to the separation-extraction device 82. The separation-extraction device 82 is configured to separate the liquid developer transported from the first recovery container 279 into the toner and the liquid carrier, and to extract the toner and the liquid carrier. Also, the separation-extraction device 82 is connected to the carrier tank CY through a flow path R10. Furthermore, a pump P10 is attached to the flow path R10. The pump P10 is configured to send the liquid carrier separated by the separation-extraction device 82 to the carrier tank CY.

The separation-extraction device 82 mainly includes an electrode roller 82a, a blockage roller 82b, a liquid container 82c, and a cleaning blade 82d. In FIG. 3, the electrode roller 82a is configured to rotate in the counter-clockwise direction. The blockage roller 82b makes contact with the electrode roller 82a. In FIG. 3, the blockage roller 82b is configured to rotate in the clockwise direction. Additionally, a small gap is produced between the liquid container 82c and the electrode roller 82a. The cleaning blade 82d makes contact with the electrode roller 82a. At least the surfaces of the electrode roller 82a, the blockage roller 82b, and the liquid container 82c are formed by a member that voltage is applicable (e.g., metal or conductive resin). Also, a second density detection device 60 is connected to the separation-extraction device 82. The second density detection device 60 is configured to detect the density of the toner included in the liquid carrier extracted by the separation-extraction device 82. The second density detection device 60 is connected to the upstream of the separation-extraction device 82 (i.e., the flow path R9) through the flow path R12. Also, the second density detection device 60 is connected downstream of the separation-extraction device 82 (i.e., the flow path R10) through a flow path R11. Furthermore, a pump P11 is attached to the flow path R11. The pump P11 is configured to send the liquid developer discharged from the separation-extraction device 82 to the second density detection device 60. Furthermore, a pump P12 is attached to the flow path R12. The pump P12 is configured to send the liquid developer back to the upstream of the separation-extraction device 82 after the density of the liquid developer is measured by the second density detection device 60.

1-3 First Density Detection Device 15

Figure 4:
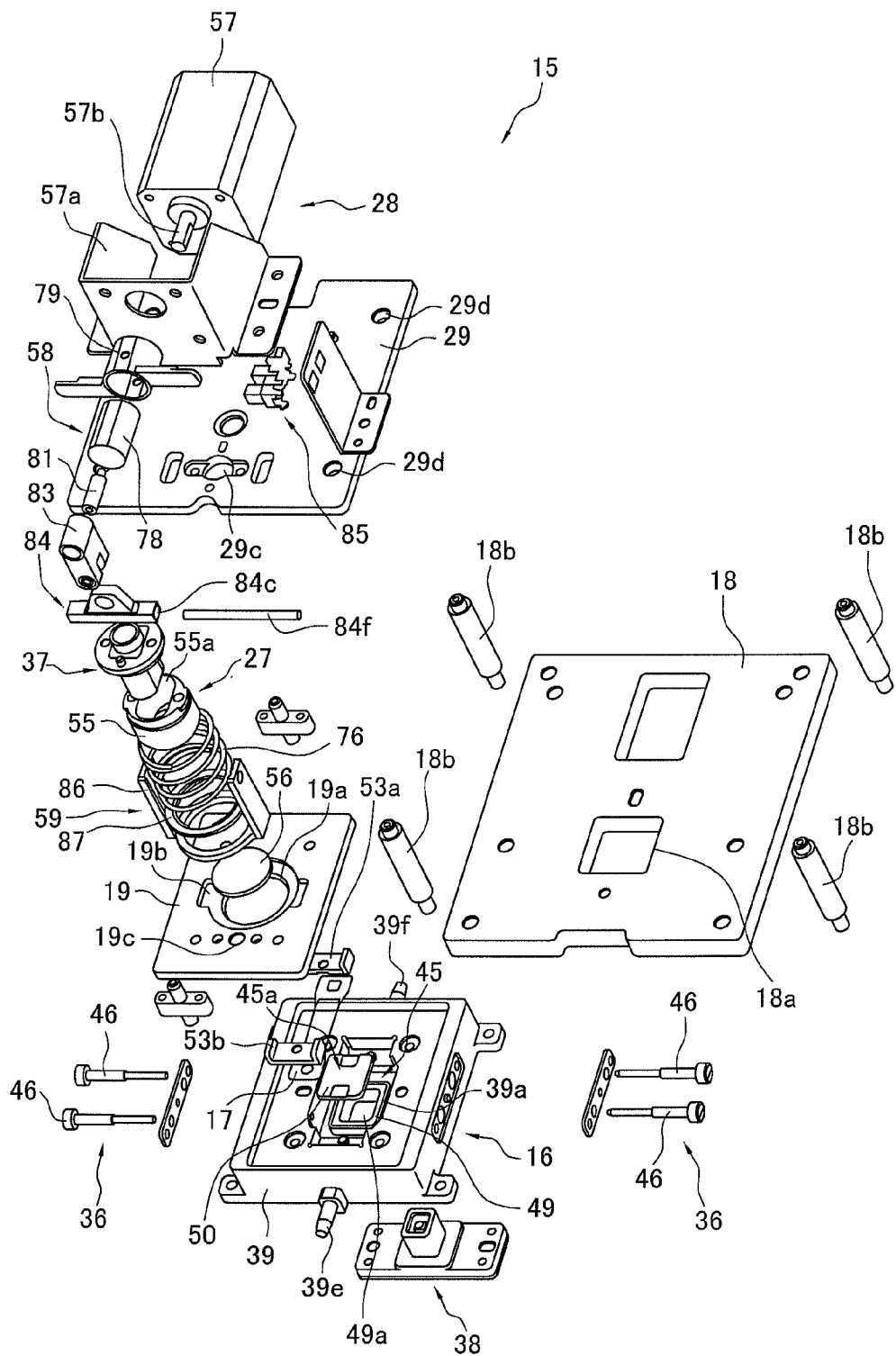
FIG. 4 is an exploded perspective view of a first density detection device of the color printer.
Figure 5:
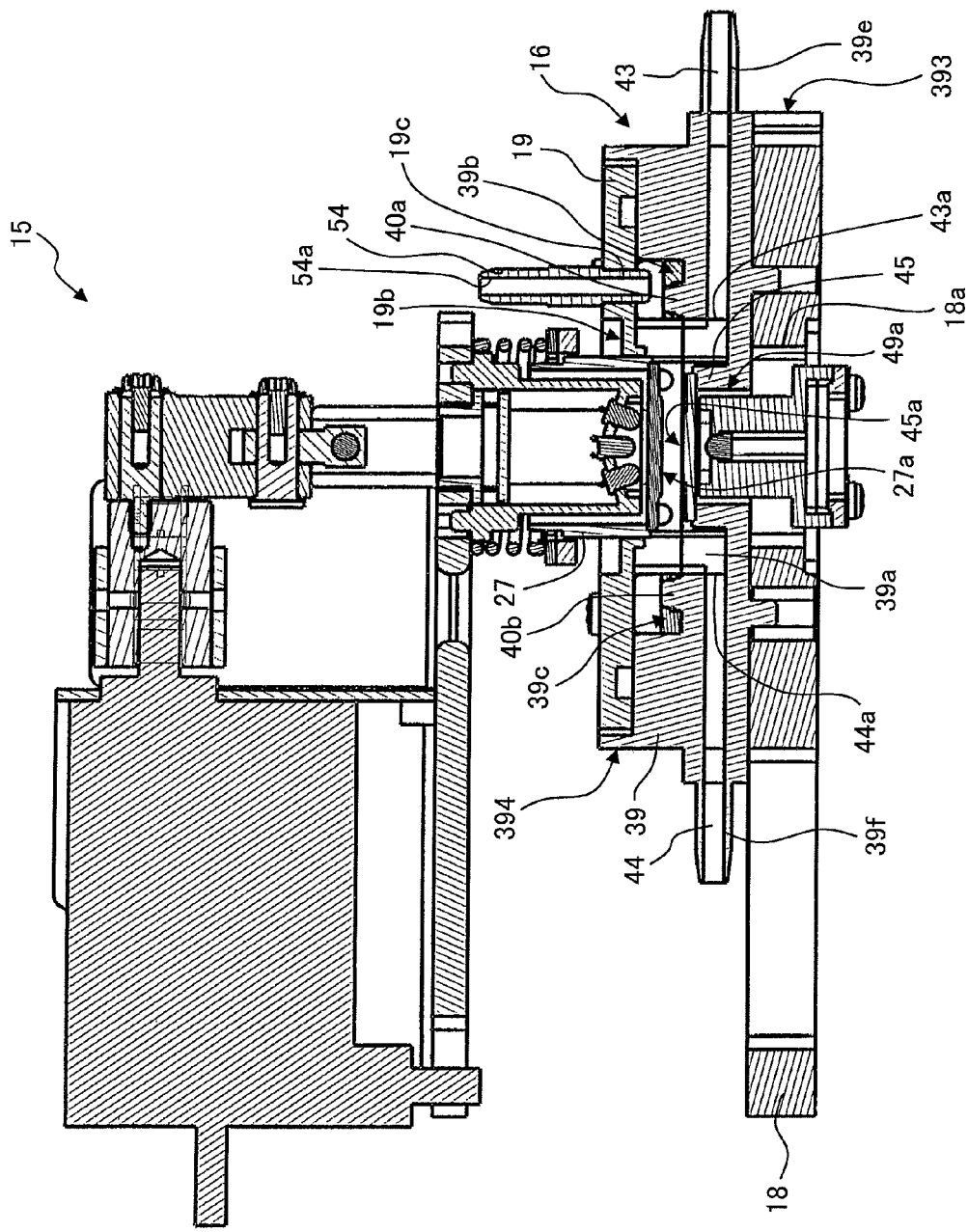
FIG. 5 is a cross-sectional side view of the first density detection device.

FIG. 4 is an exploded perspective view of the first density detection device 15, and FIG. 5 is a cross-sectional side view thereof. The first density detection device 15 includes a casing unit 16, a spacer 17, a first base member 18, a sealing member 19, a movable member 27, a drive mechanism 28, a second base member 29, a regulation member 36, a light-emitting member 37, and a light-receiving member 38.

The casing unit 16 includes a casing 39, an inflow path 43 (see FIG. 5), an outflow path 44 (see FIG. 5), and a base 45.

The casing 39 includes an internal space S1 or recess 39a to make or to allow the liquid developer pass through. As illustrated in a top view of the casing 39 of FIG. 6, the recess 39a is formed on the center part of the top side of the casing 39. The recess 39a is dented downward. The aforementioned internal space S1 is surrounded by the outer periphery of the recess 39a. Therefore, the internal space S1 or recess 39a is opened upward. In other words, an opening is formed in the top side of the casing 39 to communicate with the internal space S1.

Furthermore, a first fixation part 39b and a second fixation part 39c are formed on the lateral sides of the recess 39a to fix the spacer 17. The first and second fixation parts 39b and 39c are dented downward from the top side of the casing 39.

Additionally, a protrusion 40a is provided on the bottom of the first fixation part 39b while a protrusion 40b is provided on the bottom of the second fixation part 39c. The protrusions 40a and 40b extend upward. The first fixation part 39b is located on the inflow path 43 side of the recess 39a. The second fixation part 39c is located on the outflow path 44 side of the recess 39a. Also, as illustrated in FIG. 5, the bottom sides of the first and second fixation parts 39b and 39c are positioned on the same height as a top side 45a of the base 45. Note the first and second fixation parts 39b and 39c make up a fixation section.

The casing 39 includes four lateral sides (i.e., first, second, third, and fourth lateral sides 391, 392, 393, and 394). The first lateral side 391 is opposed to the second lateral side 392 whereas the third lateral side 393 is opposed to the fourth lateral side 394. The first and second lateral sides 391 and 392 respectively include a plurality of through-holes 39d. The through-holes 39d are communicated with the internal space S1. Specifically, two through-holes 39d are horizontally aligned in the first lateral side 391. Similarly, two through-holes 39d are horizontally aligned in the second lateral side 392. The through-holes 39d formed in the first lateral side 391 and those in the second lateral side 392 are respectively opposed to each other. Pin members 46 (to be described) are inserted into the through-holes 39d (see FIG. 11).

The inflow path 43 (see FIG. 5) is a flow path to make the liquid developer flow into the internal space S1. An end of the inflow path 43 is communicated with the internal space S1 through an inlet 43a facing the internal space S1. The inlet 43a is provided in the lower part of the lateral side of the recess 39a. The other end of the inflow path 43 is communicated with an opening formed in the tip of an inflow part 39e. The inflow part 39e protrudes from the third lateral side 393 of the casing 39. The inflow part 39e is connected to the flow path R4 to connect the pump P4 (see FIG. 3) and the first density detection device 15.

The outflow path 44 is a flow path to make the liquid developer flow out of the internal space S1. An end of the outflow path 44 is communicated with the internal space S1 through an outlet 44a facing the internal space S1. The outlet 44a is provided in the lower part of the lateral side of the recess 39a. However, the outlet 44a is positioned opposite to the inlet 43a. The other end of the outflow path 44 is communicated with an opening formed in the tip of an outflow part 39f. The outflow part 39f protrudes from the fourth lateral side 394 of the casing 39. The outflow part 39f is connected to the flow path R4 to connect the regulation container 272 (see FIG. 3) and the first density detection device 15.

Figure 6:
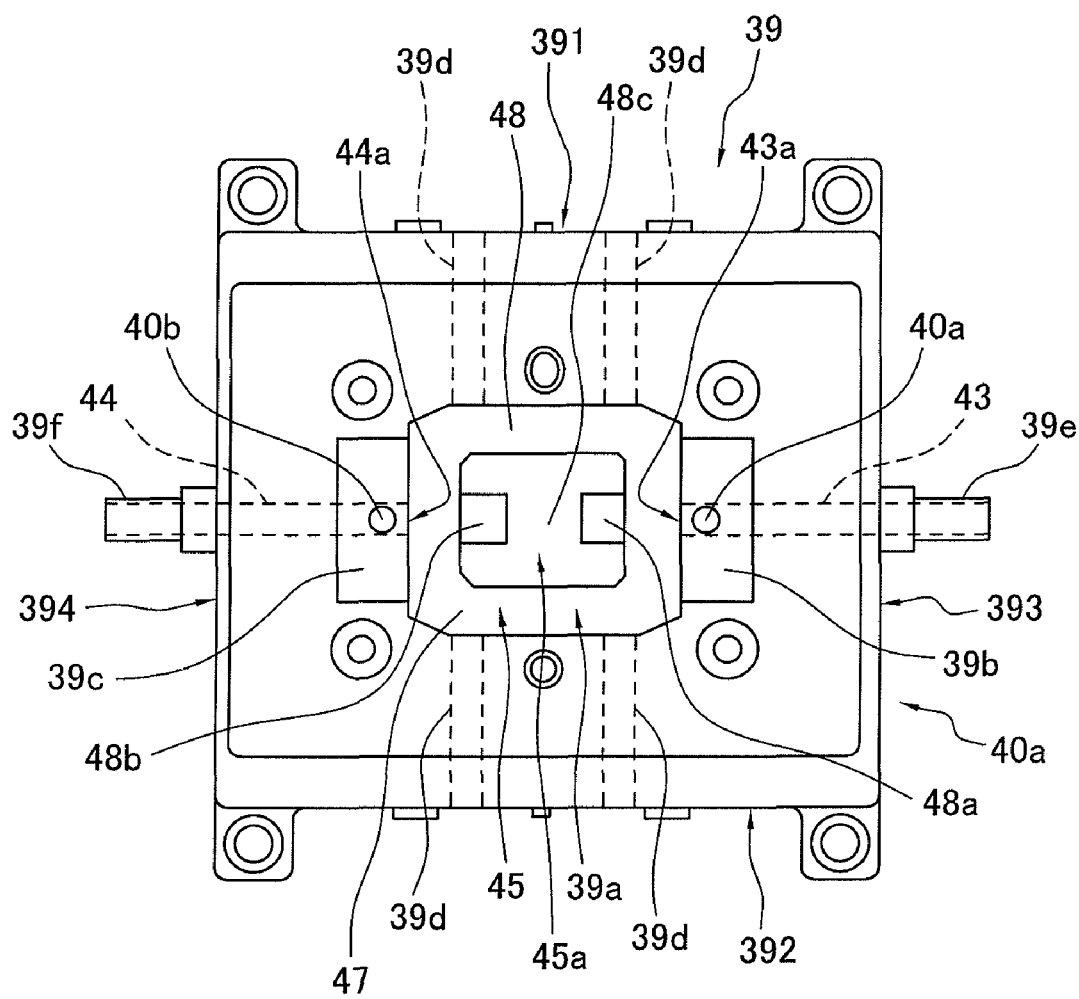
FIG. 6 is a top view of a casing of the first density detection device.

The base 45 protrudes upward from the bottom side of the recess 39a in the internal space S1. As illustrated in FIG. 6, the base 45 is arranged in approximately the center part of the internal space S1. The base 45 is arranged between the first and second fixation parts 39b and 39c. Additionally, the base 45 is arranged between the inlet 43a and the outlet 44a. The base 45 blocks liquid flowing from the inlet 43a. The height of the base 45 is suitably set in accordance with a variety of factors (e.g., viscosity of and the amount of the liquid developer). For example, it is preferably set to approximately 6.5 mm for this embodiment. Flow paths 47 and 48 are provided around the base 45 to connect the inlet 43a and the outlet 44a.

The top side 45a of the base 45 is a horizontally-arranged flat side. The top side 45a functions as a first liquid layer formation surface to form a liquid developer layer. As illustrated in FIG. 5, the top side 45a of the base 45 is positioned above the inlet 43a and the outlet 44a. The top side 45a is also positioned at the same height as the bottom sides of the first and second fixation parts 39b and 39c. Furthermore, as illustrated in FIG. 6, a pair of grooves 48a and 48b is formed on the top side 45a of the base 45. The grooves 48a and 48b are separated a predetermined distance in the direction connecting the inlet 43a and the outlet 44a. In other words, the grooves 48a and 48b are arranged along the flow direction of the liquid flowing into the internal space Si from the inlet 43a. The groove 48a reaches an edge of the top side 45a on the inlet 43a side whereas the groove 48b reaches an edge of the top side 45a on the outlet 44a side. A part of the top side 45a interposed between the grooves 48a and 48b is a transmission part 48c. The transmission part 48c allows the light irradiated from an after-mentioned light-emitting member 37 to pass through it. As illustrated in FIG. 4, the base 45 is made up of a base body 49 and a top 50. The base body 49 and the top 50 are separately provided members. The base body 49 includes a through-hole 49a. The through-hole 49 penetrates the base body 49 and reaches the bottom side of the casing 39. The top 50 is attached to the base body 49 to cover the upper side of the through-hole 49a. The top 50 is preferably made of translucent material (e.g., transparent resin).

The spacer 17 illustrated in FIG. 4 makes contact with a bottom side 27a of the movable member 27 and the top side 45a of the base 45. Accordingly, the bottom side 27a and the top side 45a are separated at a predetermined small distance through the spacer 17. The spacer 17 is a thin metal plate member. Thickness of the spacer is uniformly formed in thickness of approximately tens of micrometers. Thickness of the spacer 17 may be set in accordance with colors of the liquid developer (i.e., target of density detection) and settings of image formation.

Figure 7:
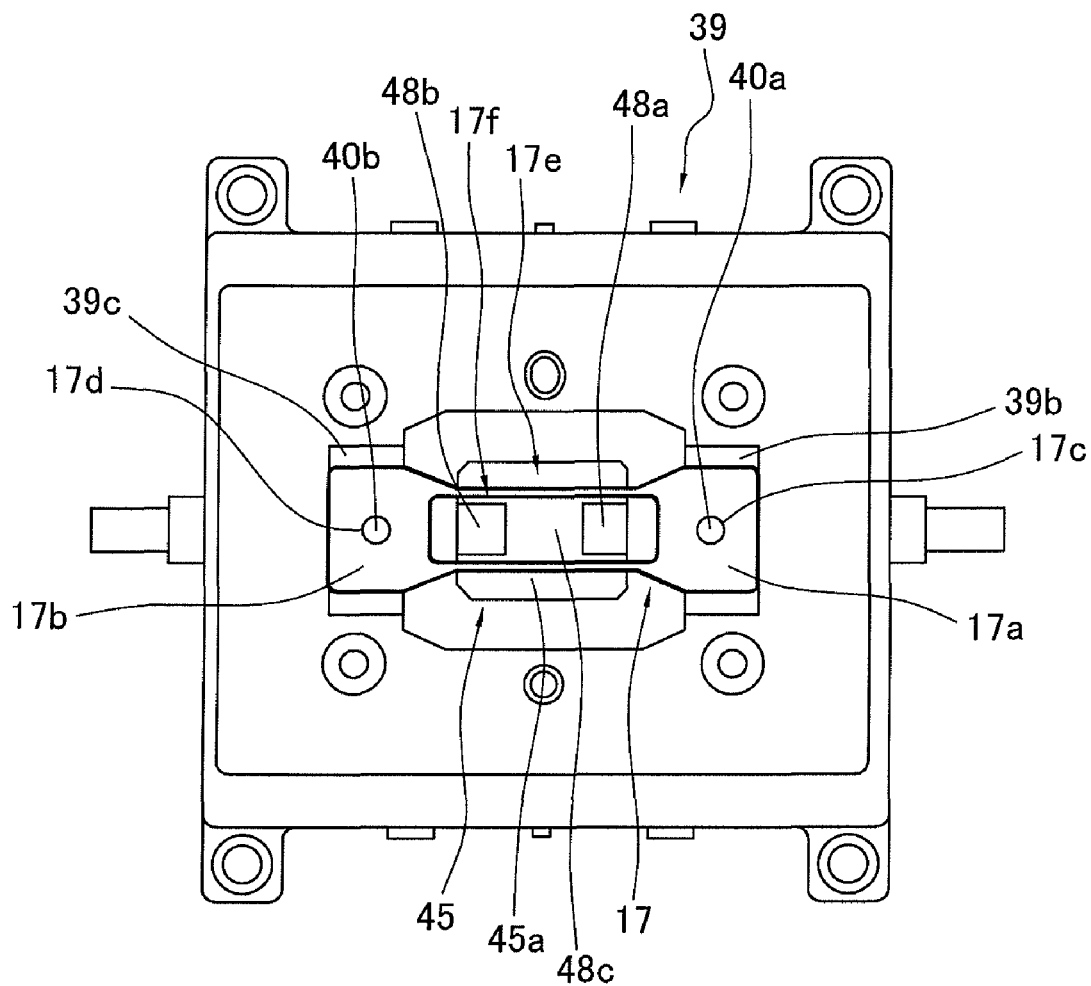
FIG. 7 is a top view of the casing with a spacer.

As illustrated in FIG. 7, width of longitudinal ends 17a and 17b of the spacer 17 is greater than that of a center part 17e of the spacer 17. The longitudinal end 17a is fixed to the first fixation part 39b whereas the longitudinal end 17b is fixed to the second fixation part 39c. Specifically, a through-hole 17c is formed in the longitudinal end 17a whereas a through-hole 17d is formed in the longitudinal end 17b. The protrusion 40a of the first fixation part 39b is inserted into the through-hole 17c whereas the protrusion 40b of the second fixation part 39c is inserted into the through-hole 17d. A fixation member 53a (see FIG. 4) is subsequently attached to the longitudinal end 17a of the spacer 17 from above whereas a fixation member 53b (see FIG. 4) is attached to the longitudinal end 17b of the spacer 17 from above. Consequently, the longitudinal ends 17a and 17b are fixed to the first and second fixation parts 39b and 39c, respectively.

As described above, when the longitudinal ends 17a and 17b of the spacer 17 are fixed to the first and second fixation parts 39b and 39c, respectively, the center part 17e of the spacer 17 makes contact with the top side 45a of the base 45. Furthermore, a through-hole 17f is formed in the center part 17e. The through-hole 17f extends along the longitudinal direction of the spacer 17. The through-hole 17f is opposed to the grooves 48a and 48b and the transmission part 48c of the base 45. Longitudinal length of the through-hole 17f is longer than the corresponding horizontal length of the base 45. Therefore, when the spacer 17 is fixed to the base 45, the through-hole 17f protrudes from toward the inlet 43a and the outlet 44a from the base 45. With this structure, part of the liquid developer flowing into the internal space S1 from the inlet 43a flows through the groove 48a from the through-hole 17f, runs on the top side 45a of the base 45, flows from the top side 45a to the groove 48b, and finally reaches the outlet 44a. In FIG. 7, the spacer 17 is bolded for easy visualization.

The first base member 18 illustrated in FIG. 4 is a plate member to support the casing unit 16. The casing unit 16 is fixed to the top side of the first base member 18. The first base member 18 includes a through-hole 18a. The through-hole 18a penetrates the first base member 18 in a plate thickness direction. The through-hole 18a is opposed to the through-hole 49a in the interior of the base body 49.

The sealing member 19 includes a through-hole 19a. The movable member 27 is inserted into the through-hole 19a. The through-hole 19a is formed in the same shape as the outer shape of the movable member 27. Accordingly, a brim 19a' (FIG. 12) of the through-hole 19a prevents horizontal movement of the movable member 27. In other words, the movable member 27 is guided up and down by the sealing member 19, and the through-hole 19a acts as a or a part of a restriction member provided in the sealing member 19. Furthermore, the sealing member 19 is attached to the top side of the casing 39 to infill the opening of the casing 39 together with the movable member 27. With this structure, the internal space S1 of the casing 39 is sealed. In other words, it is possible to prevent the liquid developer flowing through the internal space S1 of the casing 39 from leaking out of the first density detection device 15. The surrounding part of the through-hole 19a on the top side of the sealing member 19 includes a recess 19b. The recess 19b fits with the outer shape of the bottom side of a second lift member 86 to be described. The bottom side of the second lift member 86 is inserted into the recess 19b. Also, a through-hole 19c is formed lateral to the recess 19b. A liquid regulation part 54 (see FIG. 5) is attached to the through-hole 19c. The through-hole 19c penetrates the sealing member 19 in an opposed position to the aforementioned first fixation part 39b. As illustrated in FIG. 5, the liquid regulation part 54 includes a flow path 54a in its interior. The liquid developer passes through the flow path 54a. When the internal space S1 becomes short of the liquid developer, the liquid developer is supplied to the internal space S1 through the liquid regulation part 54. The flow path 54a is connected to a flow path branching from the flow path R4 (not illustrated in the figure). Additionally, a pump (not illustrated in the figure) is attached to the flow path. When the internal space S1 becomes short of the liquid developer, the liquid developer is transported to the internal space S1 by the agency of the pump.

As illustrated in FIG. 5, the movable member 27 has the bottom side 27a. The bottom side 27a is arranged above the base 45, and is opposed to the top side 45a of the base 45. The movable member 27 is configured to move, and therefore the bottom side 27a is positioned close to and away from the top side 45a of the base 45. The bottom side 27a of the movable member 27 functions as a second liquid layer formation surface to form a liquid developer layer. As illustrated in FIG. 4, the movable member 27 includes a movable body 55 and a bottom 56. The movable body 55 and the bottom 56 are separately provided.

Figure 8:
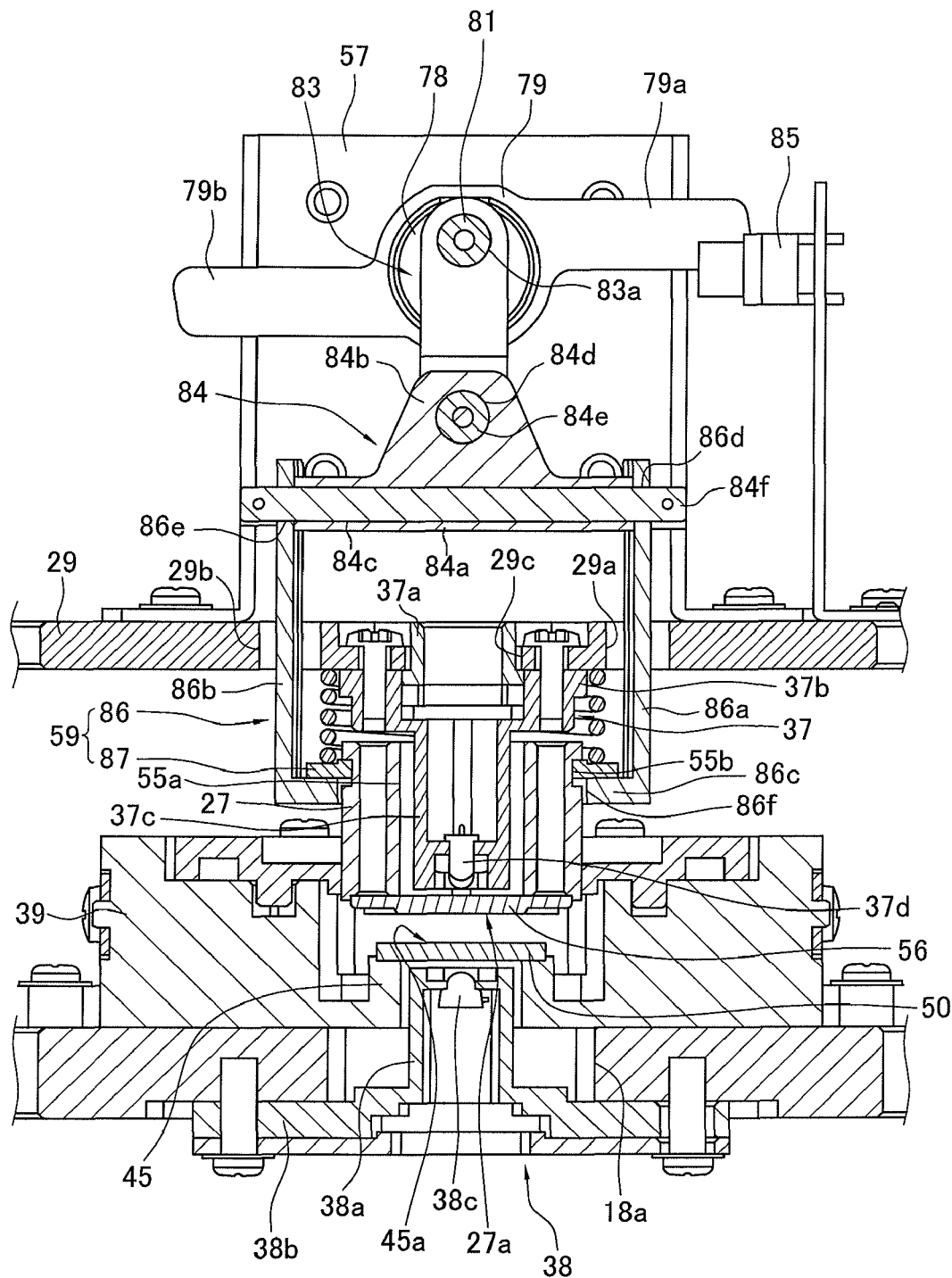
FIG. 8 is a cross-sectional side view of the first density detection device in a stand-by condition seen in a cross-section perpendicular to the cross-section of FIG. 5.

The movable body 55 is formed in a cylindrical shape. The movable body 55 includes a through-hole 55a in its interior. The through-hole 55a axially penetrates the movable body 55. As illustrated in FIG. 8, a groove (interlocked part) 55b is formed on the upper part of the outer periphery of the movable body 55. The groove 55b is arranged along the circumferential direction of the movable body 55.

The bottom 56 is attached to the movable body 55 to cover the bottom side of the through-hole 55a. The bottom side 27a of the bottom 56 functions as the aforementioned second liquid layer formation surface. The bottom 56 is preferably made of translucent material (e.g., transparent resin).

Referring to FIG. 4, the drive mechanism 28 is configured to move the movable member 27 up and down. The drive mechanism 28 includes a drive motor 57, a link mechanism 58, a retainer 59, and an urging member 76.

The drive motor 57 is controlled by a control unit 77 (see FIG. 3). The drive motor 57 generates a driving force to move the movable member 27. The drive motor 57 is fixed to the top side of the second base member 29 through a bracket 57a.

The link mechanism 58 is configured to transmit the driving force generated by the drive motor 57 to the movable member 27 through the retainer 59. The link mechanism 58 includes an inner cylindrical part 78, an outer cylindrical part 79, an eccentric shaft 81, a link arm 83, and a first lift member 84.

The inner cylindrical part 78 is fixed to a rotation shaft 57b of the drive motor 57.

Figure 9:
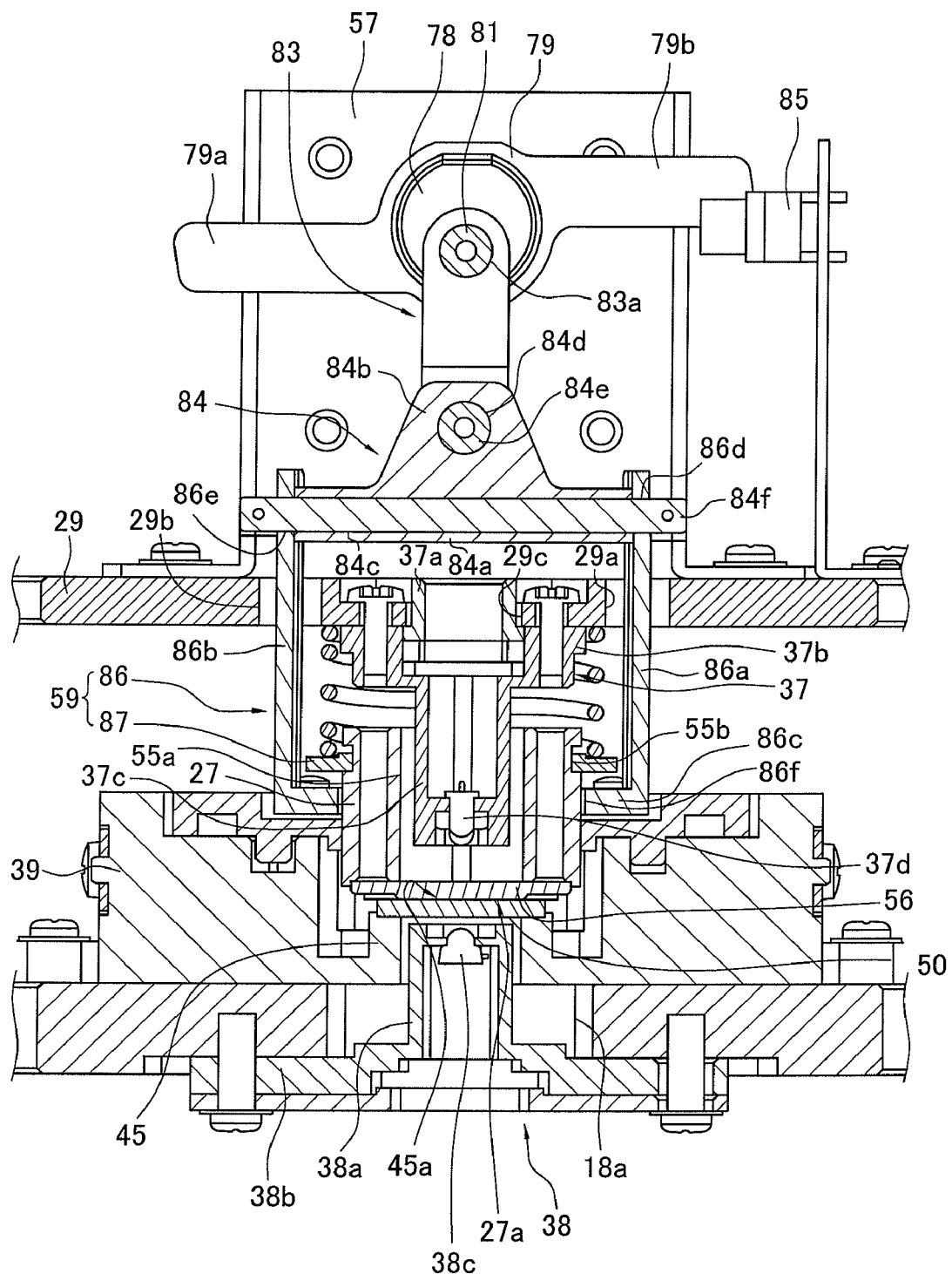
FIG. 9 is a cross-sectional side view of the first density detection device in a detection condition seen in a cross-section perpendicular to the cross-section of FIG. 5.
Figure 10:
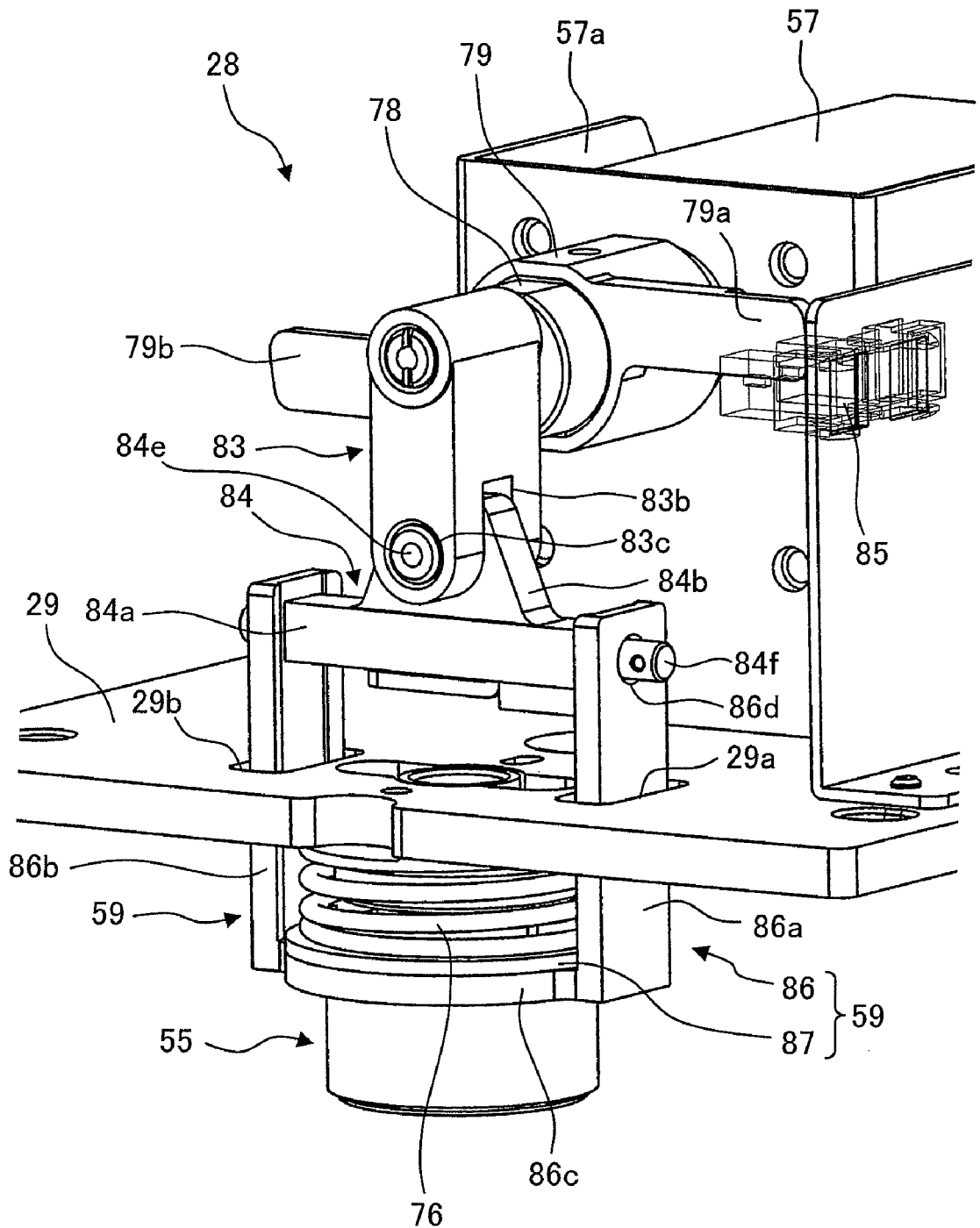
FIG. 10 is a perspective view of a driving mechanism of the first density detection device.

As illustrated in FIGS. 8 to 10, the outer cylindrical part 79 is attached to the inner cylindrical part 78 to cover the outer periphery of the inner cylindrical part 78. FIGS. 8 and 9 are cross-sectional side views of the first density detection device 15 seen from a perpendicular cross-section to the cross-section of FIG. 5. As illustrated below, FIG. 8 illustrates the first density detection device 15 in the stand-by condition whereas FIG. 9 illustrates the first density detection device 15 in the detection condition. Also, FIG. 10 is a perspective view of the drive mechanism 28.

The outer cylindrical part 79 is provided with a pair of blades 79a and 79b. The blades 79a and 79b protrude from the outer periphery of the outer cylindrical part 79. The pair of blades 79a and 79b are arranged in parallel to each other. The blades 79a and 79b are configured to rotate in conjunction with rotation of the drive motor 57. Furthermore, a position detection sensor 85 is provided to detect actions of the blades 79a and 79b. The position detection sensor 85 is opposed to the passage position of the blades 79a and 79b. The control unit 77 (see FIG. 3) is configured to detect a position of the movable member 27 based on the detection result by the position detection sensor 85.

The eccentric shaft 81 is fixed to the end surface of the inner cylindrical part 78. The eccentric shaft 81 is arranged eccentric to the rotational axis of the inner cylindrical part 78. Note that the term "axial direction" hereinafter means the axial direction of the eccentric shaft 81, that is, a parallel direction to the axial direction of the rotation shaft 57b of the drive motor 57.

The link arm 83 is formed in a vertically-extending shape. The upper end of the link arm 83 includes a through-hole 83a. The through-hole 83a axially penetrates the link arm 83. The eccentric shaft 81 is inserted into the through-hole 83a, and the link arm 83 is rotatably attached to the eccentric shaft 81. Additionally, an E-shaped retainer ring is attached to the tip of the eccentric shaft 81 on the link arm 83 side to prevent the link arm 83 from dropping off the eccentric shaft 81. As illustrated in FIG. 10, the lower end of the link arm 83 includes a recess 83b. The recess 83b is dented upward from the bottom of the link arm 83. Furthermore, the lower end of the link arm 83 includes a through-hole 83c. The through-hole 83c axially penetrates the link arm 83 and is perpendicular to the recess 83b.

The first lift member 84 includes a horizontal part 84a and an attachment part 84b. The horizontal part 84a is formed in a horizontally-extending stick shape. The attachment part 84b is attached to the top side of the horizontal part 84a. The horizontal part 84a includes a through-hole 84c. The through-hole 84c penetrates the horizontal part 84a along the longitudinal direction. The attachment part 84b includes a through-hole 84d. The through-hole 84d axially penetrates the attachment part 84b. As illustrated in FIG. 10, the attachment part 84b is inserted into the recess 83b of the link arm 83. Then, a pin member 84e is simultaneously inserted into the through-hole 84d (see FIGS. 8 and 9) of the attachment part 84*b* and the through-hole 83*c* (see FIG. 10) of the link arm 83. Additionally, an E-shaped retainer ring is attached to the both tips of the pin member 84*e* to prevent the pin member 84*e* from dropping off the link arm 83. With this structure, the first lift member 84 is rotatably attached to the link arm 83. Note that the first lift member 84 is positioned above the second base member 29.

The retainer 59 retains the movable member 27 to allow it to move freely. The retainer 59 includes the second lift member 86 and an interlocking member 87.

The second lift member 86 includes a pair of arm parts 86*a* and 86*b* and a support part 86*c*.

The arm parts 86*a* and 86*b* are vertically-extending plate members. The arm parts 86*a* and 86*b* are horizontally separated a predetermined distance. The upper end of the arm part 86*a* includes a through-hole 86*d* while the upper end of the arm part 86*b* includes a through-hole 86*e*. The through-holes 86*d* and 86*e* horizontally penetrate the arm parts 86*a* and 86*b*, respectively. The arm part 86*a* is inserted into the through-hole 29*a* formed in the second base member 29 while the arm part 86*b* is inserted into the through-hole 29*b* formed in the second base member 29. The upper ends of the arm parts 86*a* and 86*b* are positioned above the second base member 29. Furthermore, the horizontal part 84*a* of the first lift member 84 is arranged between the upper ends of the pair of arm parts 86*a* and 86*b*. Then, a pin member 84*f* is simultaneously inserted into the through-holes 86*d* and 86*e* of the arm parts 86*a* and 86*b* and the through-hole 84*c* of the horizontal part 84*a*. Accordingly, the second lift member 86 is attached to the first lift member 84. Note the pin member 84*f* includes through-holes in both tips, and stick-shaped members are pressed into the through-holes, respectively. Accordingly, the pin member 84*f* is retained.

The support part 86*c* is formed in a ring shape. The support part 86*c* supports the movable member 27 through the interlocking member 87. The support part 86*c* is arranged between the pair of arm parts 86*a* and 86*b*, and is connected to the lower ends of the arm parts 86*a* and 86*b*. As illustrated in FIGS. 8 and 9, the support part 86*c* includes a through-hole 86*f*. Inner diameter of the through-hole 86*f* is slightly greater than the outer shape of the movable member 27.

The interlocking member 87 is a ring shaped plate member. The interlocking member 87 is arranged above the support part 86*c*. The outer diameter of the interlocking member 87 is slightly less than the outer diameter of the support part 86*c*, and is greater than the inner diameter of the support part 86*c*. Additionally, the inner diameter of the interlocking member 87 is less than the outer diameter of the movable member 27, and is greater than the outer diameter of the groove 55*b* of the movable member 27. The interlocking member 87 is fitted into the groove 55*b* of the movable member 27, and is thus interlocked with the groove 55*b*. The thickness of the interlocking member 87 is less than the width (i.e., vertical dimension in this case) of the groove 55*b* of the movable member 27. In other words, the movable member 27 is not firmly fixed to the interlocking member 87, and clearance is produced between the groove 55*b* and the interlocking member 87. With this structure, the movable member 27 is configured to move up and down slightly with respect to the interlocking member 87. Also, inner diameter of the support part 86*c* is greater than the outer diameter of the groove 55*b* of the movable member 27. Accordingly, the movable member 27 is configured to pivot slightly while its axis line tilts with respect to the vertical direction.

The urging member 76 is preferably a coil spring. The urging member 76 urges the movable member 27 through the interlocking member 87. The urging member 76 is arranged between the pair of arm parts 86*a* and 86*b*. Additionally, the urging member 76 is inserted between the bottom side of the second base member 29 and the interlocking member 87. The outer diameter of the urging member 76 is less than that of the interlocking member 87. The lower end of the urging member 76 makes contact with the top side of the interlocking member 87. Also, the inner diameter of the urging member 76 is greater than outer diameter of the movable member 27. The upper end of the movable member 27 is inserted into the inside of the urging member 76. The movable member 27 is accordingly configured to move up and down in the inside of the urging member 76. The urging member 76 urges the interlocking member 87 downward (i.e., toward the spacer 17). The urging member 76 urges the movable member 27 toward the spacer 17 through the interlocking member 87 when the bottom side 27*a* of the movable member 27 makes contact with the spacer 17.

The second base member 29 supports the drive motor 57. As described above, the second base member 29 includes the pair of through-holes 29*a* and 29*b*, and the through-holes 29*a* and 29*b* vertically penetrate the second base member 29. Additionally, the arm parts 86*a* and 86*b* are inserted into the through-hole 29*a* and 29*b*, respectively. Also, the second base member 29 includes a through-hole 29*c* between the pair of through-holes 29*a* and 29*b*. An upper end 37*a* of the light-emitting member 37 (to be described) is inserted into the through-hole 29*c*. The second base member 29 is supported by the first base member 18 through a plurality of post members 18*b* (see FIG. 4). In this case, four post members 18*b* are arranged to support the four corners of the second base member 29. The upper ends of the post members 18*b* are inserted into the through-holes 29*d* formed in the second base member 29.

Figure 11:
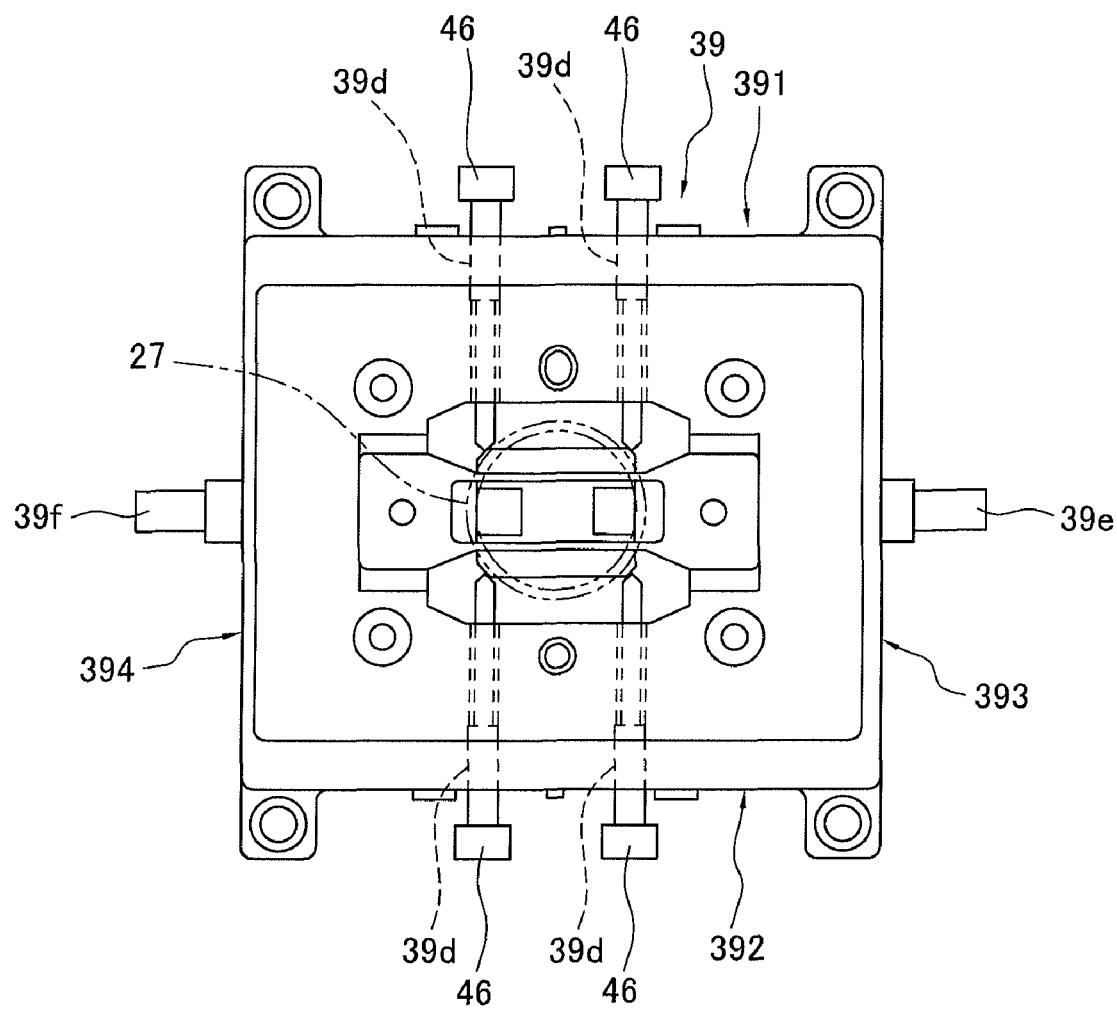
FIG. 11 is a top view of the casing illustrating a positional relation between a movable member and a regulation member.

The regulation member 36 illustrated in FIG. 4 includes a plurality of pin members 46. As illustrated in FIG. 11, the pin members 46 are inserted into the through-holes 39 formed in the first and second lateral sides 391 and 392 of the casing 39. Thus, the tips of the pin members 46 protrude into the interior space. With this structure, the pin members 46 laterally protrude toward the movable member 27 (see dashed-two dotted circular lines in FIG. 11) from the lateral sides of the movable member 27 while the bottom side 27*a* of the movable member 27 is positioned close to the top side 45*a* of the base 45. In this condition, the tips of the pin members 46 surround the movable member 27 below the sealing member 19. With this structure, the pin members 46 restrict horizontal movement of the movable member 27. Thus, the pin members 46 can also form the restriction member or part of the restriction member.

As illustrated in FIG. 8, the light-emitting member 37 is fixed to the bottom side of the second base member 29. The light-emitting member 37 is arranged between the bottom side of the second base member 29 and the movable member 27. Additionally, the light-emitting member 37 is arranged in the inside of the urging member 76. The light-emitting member 37 includes the upper end 37*a*, a flange 37*b*, a main body 37*c* and a light-emitting element 37*d*. The outer shape of the upper end 37*a* is a cylindrical shape. The upper end 37*a* is inserted into the through-hole 29*c* of the aforementioned second base member 29. The outer shape of the flange 37*b* is a disc shape. The outer diameter of the flange 37*b* is greater than that of the upper end 37*a*. The outer shape of the main body 37*c* is smaller than that of the flange 37*b*. The main body 37*c* is arranged below the flange 37*b*. The main body 37*c* is inserted into the through-hole 55*a* of the movable member 27. A light-emitting element 37*d* is arranged in the lower end of the main body 37*c*. Accordingly, the light-emitting element 37d is configured to irradiated downward. The control unit 77 (see FIG. 3) is configured to control irradiation of the light-emitting element 37d.

The light-receiving member 38 is arranged below the top side 45a of the base 45. The light-receiving member 38 includes a main body 38a, a flange 38b and a light-receiving element 38c. The main body 38a is inserted into the through-hole 18a of the aforementioned first base member 18. The main body 38a is arranged in the inside of the base 45. A light-receiving element 38c is arranged in the upper end of the main body 38a. The light-receiving element 38c receives light irradiated by the light-emitting member 37. The light irradiated by the light-emitting element 37d transmits through the bottom 56 of the movable member 27, the interior space of the casing 39 and the top 50 of the base 45, and finally reaches the light-receiving element 38c. The light-receiving element 38c converts the received light into voltage. The control unit 77 (see FIG. 3) receives a signal from the light-receiving element 38c. Then, the control unit 77 calculates the light attenuation rate based on intensity of the light irradiated by the light-emitting element 37d and intensity of the light received by the light-receiving element 38c, and obtains the density of the liquid developer based on the attenuation rate. Thus, the light-receiving member 38, the light-emitting member 37, and the control unit 77 make up a density detection section to detect density of liquid developer.

2. Operation 2-1 Image Forming Operation

First, an image forming operation of the color printer 1 will be explained with reference to FIGS. 1 and 2. When the color printer 1 receives an instruction to form an image from a personal computer (not illustrated in the figure) connected to the color printer 1, the color printer 1 forms four-color toner images with the image formation units FB, FY, FC, and FM in accordance with the data of the target image. Specifically, an electrostatic latent image is formed on the photosensitive drum 10 based on the image data. Subsequently, the development device 14 supplies the toner to the electrostatic latent image. The toner images formed in the image formation units FB, FY, FC, and FM are transferred to the intermediate transfer belt 21 while being overlapped to each other. A color toner image is thus formed.

In synchronization with formation of the color toner image, the paper feeding roller 32 takes a sheet of paper from the paper feeding cassette 31 of the paper storage section 3. Then, the pair of separation rollers 33 transports it to the paper transportation section 6. The sheet of paper is transported to the pair of resist rollers 75 by the plurality of transportation rollers 74 of the paper transportation section 6. The pair of resist rollers 75 corrects the transportation posture of the sheet of paper and temporarily stops transportation of the sheet of paper. Then, the pair of resist rollers 75 transports the sheet of paper to the secondary transfer section 4 in synchronization with the primary transfer onto the intermediate transfer belt 21. The color toner image on the intermediate transfer belt 21 is secondarily transferred onto the sheet of paper in the secondary transfer section 4. After the secondary transfer, the sheet of paper is transported to the fixation section 5. The color toner image is subsequently fixed onto the sheet of paper by the agency of heat and pressure.

After the color toner image is fixed onto the sheet of paper, the sheet of paper is transported to the discharge section 7. The pair of discharge rollers 71 discharges the sheet of paper to the discharge tray 72 provided on the top of the color printer 1.

After the secondary transfer, the liquid developer remaining on the intermediate transfer belt 21 is removed by the cleaning roller 22a and the cleaning blade 22b of the cleaning unit 22 of the intermediate transfer belt 21.

2-2. Circulation Operation of Liquid Developer

Next, an operation to supply the liquid developer to the development device 14, that is, an operation of circulating the liquid developer, will be hereinafter explained with reference to FIG. 3.

In the image forming operation, the remaining liquid developer on the development roller 141 without being supplied to the photosensitive drum 10 is scraped by the development cleaning blade 145. The scraped liquid developer is subsequently recovered by the recovery container 271 through the flow path R1 by the agency of the pump P1. Additionally, the liquid developer received by the development container 140 is sent to the second recovery container 271 through the flow path R2 by the agency of the pump P5. When the regulation container 272 becomes out of the liquid developer, the liquid developer is supplied to the regulation container 272 from the second recovery container 271 through the flow path R3 by the agency of the pump P2. Also, the remaining liquid developer on the photosensitive drum 10 without being transferred onto the intermediate transfer belt 21 is scraped by the cleaning blade 262, and is stored in the first recovery container 279. Furthermore, both the aforementioned liquid developer and the liquid carrier removed from the intermediate transfer belt 21 by the liquid carrier removal roller 30 are recovered by the first recovery container 279.

The liquid developer recovered by the first recovery container 279 is transported to the separation-extraction device 82 through the flow path R9 by the agency of the pump P9. Then, the separation-extraction device 82 executes separation-extraction processing to separate the liquid developer in the toner and the liquid carrier and separately extracts them.

In the separation-extraction processing, the pump P9 is firstly activated. Accordingly, the liquid developer is injected into the space between the electrode roller 82a and the liquid container 82c. In this case, the electrode roller 82a and the blockage roller 82b rotate while a voltage of −500V is applied to the electrode roller 82a and a voltage of +500V is applied to the blockage roller 82b and the liquid container 82c by a voltage application device 69, for instance. Accordingly, the toner in the liquid developer is attracted and attached to the surface of the electrode roller 82a. Only the toner attached to the electrode roller 82a is allowed to pass the press-contact portion between the electrode roller 82a and the blockage roller 82b. Then the passed toner is removed from the surface of the electrode roller 82a by the cleaning blade 82d. Consequently, the liquid carrier is extracted in the space between the electrode roller 82a and the liquid container 82c. After extraction of the liquid carrier is executed for a predetermined period of time, the liquid carrier extracted by the separation-extraction device 82 is transported to the second density detection device 60 through the flow path R11 by the agency of the pump P11. The second density detection device 60 subsequently detects the density of the toner in the transported liquid carrier. When toner density in the extracted liquid carrier is greater than predetermined value, the extracted liquid carrier is sent back to the separation-extraction device 82 through the flow path R12 by the agency of the pump P12. The separation-extraction device 82 executes separation-extraction processing again. On the other hand, when toner density in the extracted liquid carrier is equal to or less than the predetermined value, the extracted liquid carrier is sent to the carrier tank CY through the flow path R10 by the agency of the pump P10.

Also, the first density detection device 15 detects the density of the liquid developer stored in the regulation container 272, and the liquid developer in the regulation container 272 is regulated. When the density of the liquid developer in the regulation container 272 is higher than the predetermined range, the liquid carrier is supplied to the regulation container 272 from the carrier tank CY through the flow path R5 by the agency of the pump P3. On the other hand, when the density of the liquid developer in the regulation container 272 is lower than the predetermined range, the liquid developer having a higher density than the liquid developer to be used in the development device 14 is supplied to the regulation container 272 from the toner tank TY through the flow path R6 by the agency of the pump P8. The density detection operation by the first density detection device 15 will be hereinafter explained in detail.

The density-adjusted liquid developer is supplied to the reserve tank 277 from the regulation container 272 through the flow path R7 by the agency of the pump P6 as necessary. Also, the liquid developer stored in the reserve tank 277 is sent to the supply nozzle 278 through the flow path R8 by the agency of the pump P7, and is then supplied to the development device 14 from the supply nozzle 278.

2-3. Operation for Detecting Density of Liquid Developer by First Density Detection Device 15

The first density detection device 15 is set to be in a stand-by condition while an operation of detecting density of the liquid developer is not being performed. FIG. 8 illustrates the stand-by condition. In the stand-by condition, the eccentric shaft 81 is positioned in the upper center of the inner cylindrical part 78. Additionally, the interlocking member 87 is lifted upward by the second lift member 86 while resisting the urging force by the urging member 76. In other words, the interlocking member 87 is pressed to the support part 86c of the second lift member 86 by the urging member 76. In this case, the bottom side 27a of the movable member 27 does not make contact with the spacer 17. The bottom side 27a of the movable member 27 and the top side 45a of the base 45 are separated having a large gap. Furthermore, the upper end of the groove 55b of the movable member 27 and the top side of the interlocking member 87 make contact with each other (see FIG. 12). The structure prevents the urging force from being transmitted from the urging member 76 to the movable member 27. Thus the movable member 27 does not receive the urging force. Consequently, the movable member 27 is interlocked with the interlocking member 87, but the movable member 27 is configured to move freely within predetermined range.

When the first density detection device 15 executes an operation of detecting density of the liquid developer, the pump P4 (see FIG. 3) is activated and the liquid developer accordingly flows into the interior space of the first density detection device 15. In this case, the liquid developer flows into the interior space from the inlet 43a (see FIG. 5). Part of the liquid developer subsequently runs on the base 45, passes through the top side 45a of the base 45, and is finally discharged from the outlet 44a. On the other hand, the rest of the liquid developer flows into flow paths 47 and 48 (see FIG. 6) around the base 45, and is discharged from the outlet 44a. In this case, the pump P4 is activated while density of the liquid developer is regulated in the regulation container 272. However, the pump P4 is deactivated when the density regulation is completed.

Before executing the density detection operation, the first density detection device 15 moves to a detection condition from the stand-by condition illustrated in FIG. 8. FIG. 9 illustrates the detection condition.

Here, the drive motor 57 is driven and the inner cylindrical part 78 accordingly rotates. Accordingly, the eccentric shaft 81 rotationally moves around the center of the inner cylindrical part 78 and moves to the position lower than the center of the inner cylindrical part 78. The action of the eccentric shaft 81 is transmitted to the second lift member 86 through the link arm 83 and the first lift member 84. The second lift member 86 accordingly moves downward from the position in the stand-by condition illustrated in FIG. 8. The following relates to the action of the second lift member 86 moving from the position in the stand-by position of FIG. 8 to the position in the detection condition of FIG. 9. The action will be explained with reference to FIGS. 12 to 15. Note FIGS. 12 to 15 illustrate the spacer 17 in larger scale than the actual scale for easy understanding.

Figure 12:
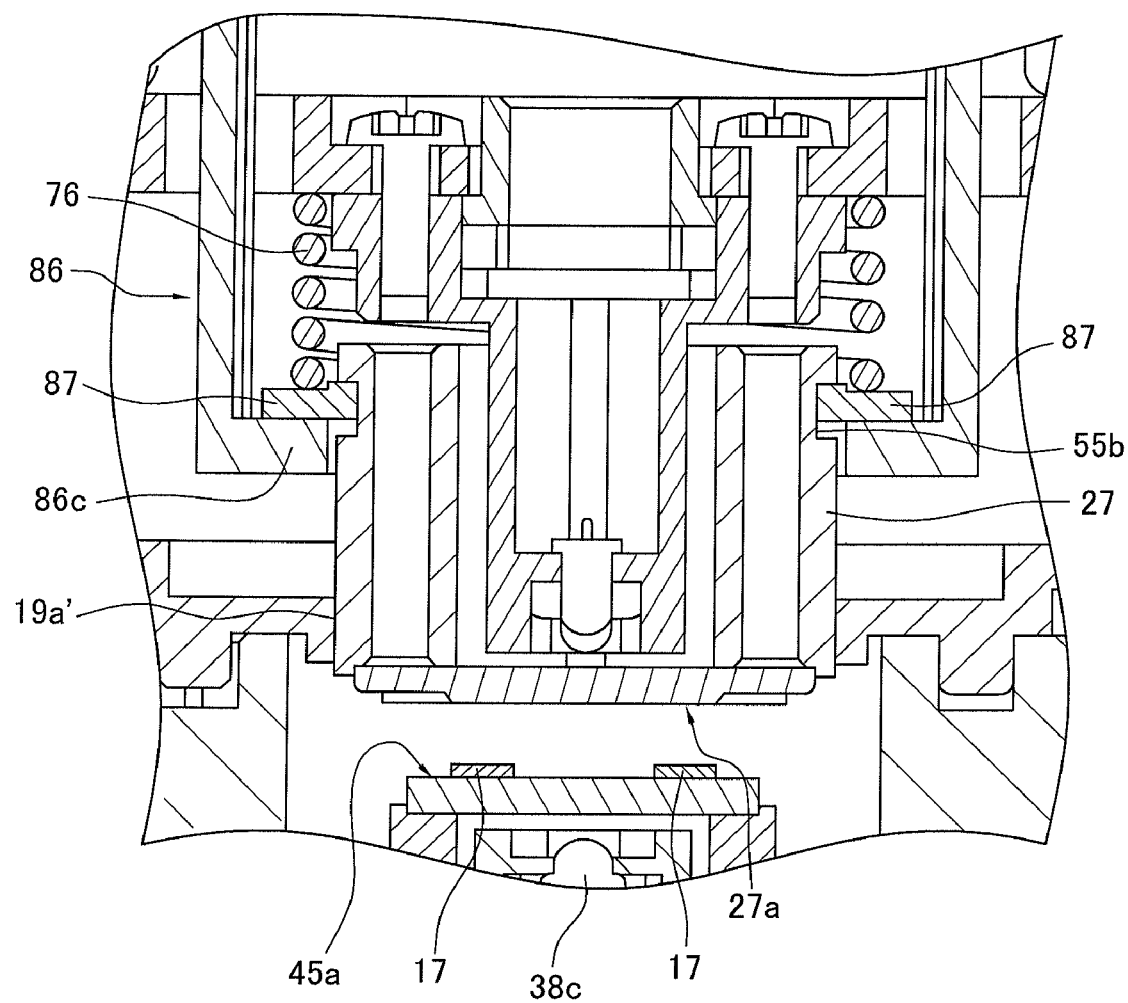
FIG. 12 is an enlarged view of a vicinity of the movable member in the stand-by condition.
Figure 13:
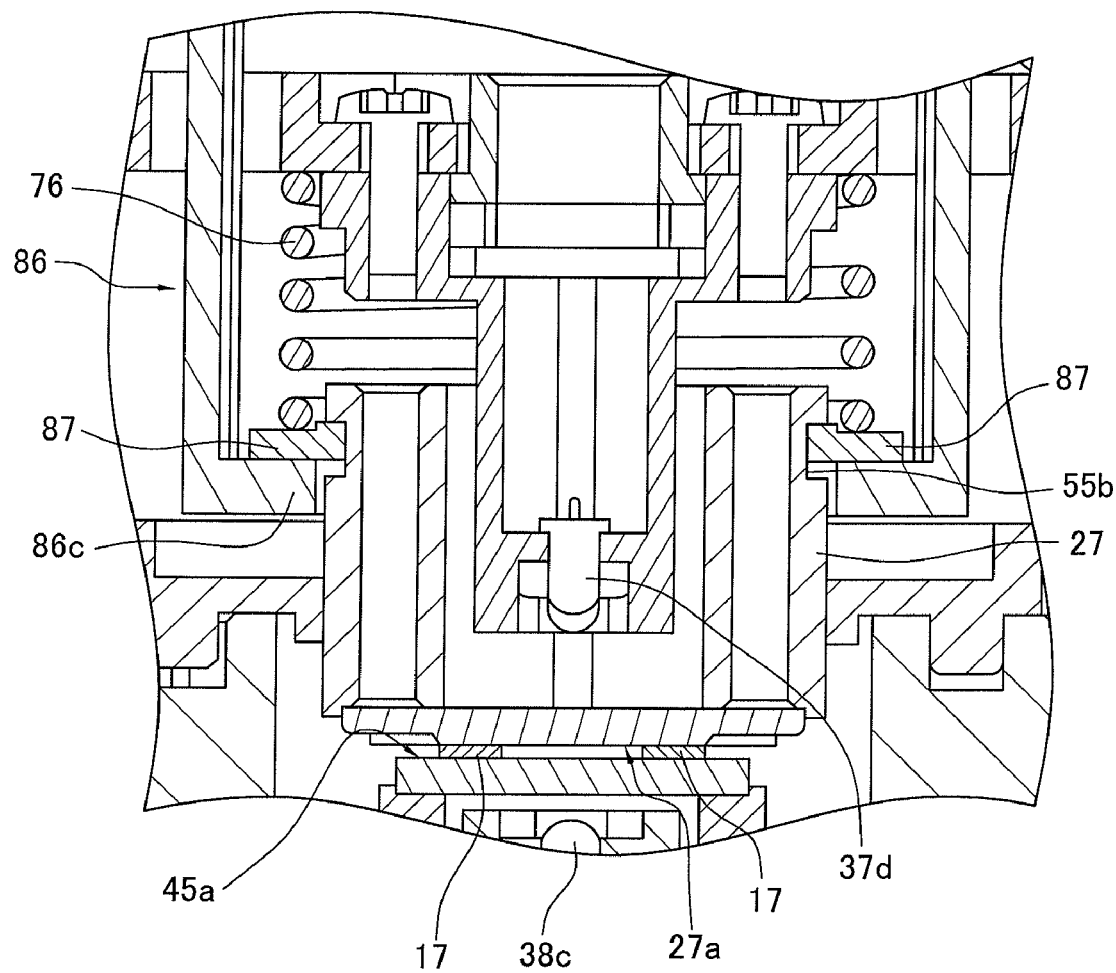
FIG. 13 is an enlarged view of the vicinity of the movable member in a transitional condition from the stand-by condition to the detection condition.
Figure 14:
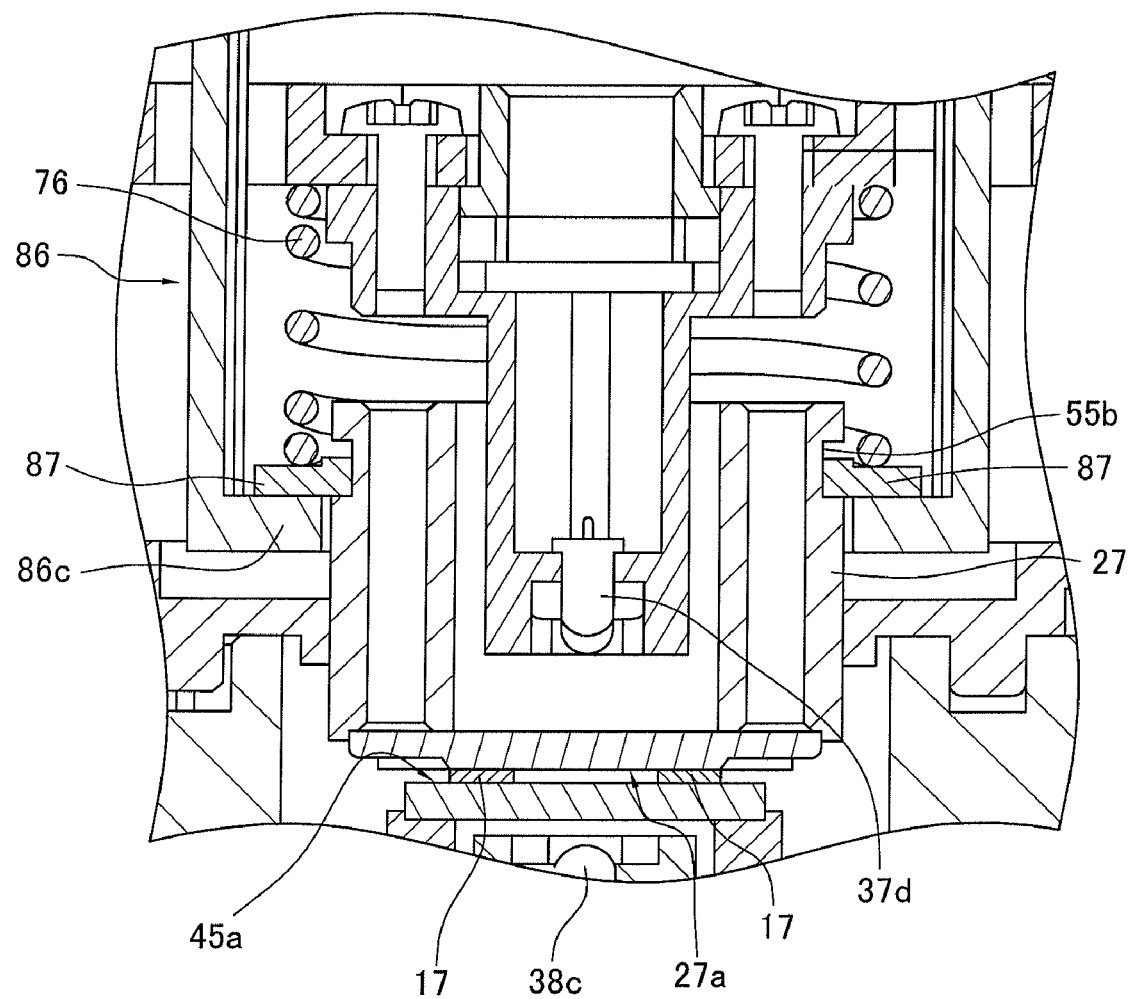
FIG. 14 is an enlarged view of the vicinity of the movable member in a transitional condition from the stand-by condition to the detection condition.

First, in the stand-by condition or the first position, the second lift member 86 is arranged in a position illustrated in FIG. 12. When the second lift member 86 moves downward from the position, the interlocking member 87 moves downward while the urging member 76 presses the interlocking member 87 toward the support part 86c of the second lift member 86. When the interlocking member 87 moves downward, the interlocking member 87 and the movable member 27 move downward. Subsequently, as illustrated in FIG. 13, the bottom side 27a of the movable member 27 makes contact with the spacer 17, and the bottom side 27a of the movable member 27 and the top side 45a of the base 45 are closely positioned through a predetermined distance. When the second lift member 86 further moves downward from the position (into the second position), the interlocking member 87 also moves downward while the second lift member 86 presses the interlocking member 87 as illustrated in FIG. 14. However, the movable member 27 is prevented from moving downward because the movable member 27 makes contact with the spacer 17. With this structure, the interlocking member 87 moves away from the upper end of the groove 55b of the movable member 27, relatively moves downward with respect to the movable member 27, and makes contact with the lower end of the groove 55b.

Figure 15:
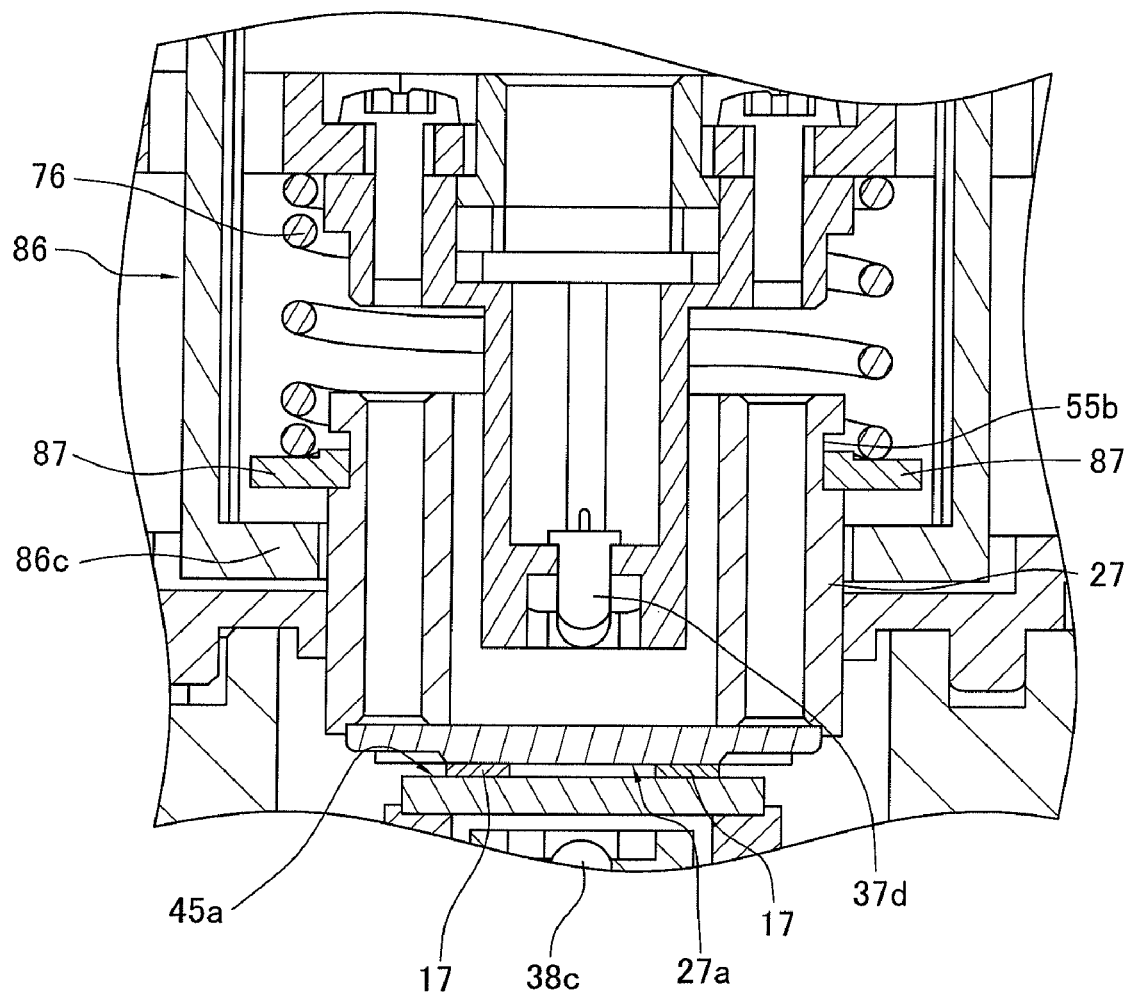
FIG. 15 is an enlarged view of the vicinity of the movable member in the detection condition.

When the second lift member 86 further moves downward, the second lift member 86 moves away from the interlocking member 87 as illustrated in FIG. 15. With this structure, the second lift member 86 releases support of the interlocking member 87. The movable member 27 accordingly receives the urging force from the urging member 76 through the interlocking member 87. In other words, the movable member 27 is urged downward (i.e., toward the spacer 17). In this case, the movable member 27 is freely-movably retained by the retainer 59. Accordingly, it is possible to regulate posture of the movable member 27 when the bottom side 27a of the movable member 27 makes contact with the spacer 17. Therefore, the bottom side 27a of the movable member 27 uniformly makes contact with the spacer 17 when the bottom side 27a of the movable member 27 is pressed to the spacer 17.

As described above, the first density detection device 15 moves to the detection condition illustrated in FIG. 9, and the bottom side 27a of the movable member 27 is positioned close to the top side 45a of the base 45 through a predetermined distance. Subsequently, the light-emitting member 37 irradiates with light a liquid developer layer formed between the bottom side 27a of the movable member 27 and the top side 45a of the base 45, and the light-receiving member 38 receives the light transmitting through the liquid developer layer. Density of the liquid developer is thus detected.

Contrary to the above, when density of the liquid developer is detected, the second lift member 86 is moved upward, and the first density detection device 15 moves to the stand-by condition from the detection condition.

3. Features

According to the first density detection device 15, the top side 45a of the base 45 is positioned above the inlet 43a and the outlet 44a, and a liquid developer layer is formed on the top side 45a. Additionally, the flow paths 47 and 48 are provided around the base 45. Accordingly, when part of the liquid developer does not run on the top side 45a, the part of the liquid developer flows into the flow paths 47 and 48 toward the outlet 44a. With this structure, it is possible to inhibit impact of the liquid developer flowing toward the outlet 44a from the inlet 43a on the liquid developer layer formed on the top side 45a of the base 45.

As described above, the spacer 17 includes the through-hole 17f (see FIG. 7). When the spacer 17 is attached to the casing unit 16, the through-hole 17f protrudes toward the inlet 43a and the outlet 44a from the base 45. Furthermore, the grooves 48a and 48b are formed on the top side 45a of the base 45, and are arranged on the inlet 43a side and the outlet 44a side, respectively. With this structure, when the liquid developer flows from the inlet 43a, the liquid developer easily runs on the top side 45a of the base 45.

Also, the spacer 17 determines distance between the bottom side 27a of the movable member 27 and the top side 45a of the base 45 in the detection condition. Additionally, the spacer 17 is separately formed from the base 45. It is accordingly possible to manufacture easily the spacer 17 with quite accurate thickness. Furthermore, the ends 17a and 17b of the spacer 17 are not directly fixed to the base 45 but fixed to the first and second fixation parts 39b and 39c, respectively. With this structure, it is not necessary to apply adhesive and the like to the top side 45a of the base 45. The structure of fixing the spacer 17 to the first and second fixation parts 39b and 39c prevents the distance between the bottom side 27a and the top side 45a from becoming uneven resulting from the effect of thickness of the adhesive.

4. Other Example Embodiments (a) In the aforementioned embodiment, the density detection device is configured to detect density of the liquid developer. However, the density detection device of the present invention is applicable to measurement of density of a variety of liquid. For example, the density detection device of the present invention may be applied to measure the amount of contaminant substances in river water or sea water in which molecular contaminant substances are dispersed, to measure the density of dye dissolving in an aqueous solution, to measure the amount of color liquid dissolving in water, to measure blood, and to measure liquid after chemical reactions.

(b) In the aforementioned embodiment, the light-emitting member 37 is provided in the movable member 27 whereas the light-receiving member 38 is provided in the base 45. However, positions of the light-emitting member 37 and the light-receiving member 38 may be opposite to each other or reversed. Also, the light-emitting member 37 and the light-receiving member 38 may be provided on the same side. In this case, either the bottom side 27a of the movable member 27 or the top side 45a of the base 45 functions as a reflection surface, and the light-receiving member 38 receives the light reflected by the reflection surface.

General Interpretation

In understanding the scope of the present invention, the term "configured" as used herein to describe a component, section or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applied to words having similar meanings such as the terms, "including," "having," and their derivatives. Also, the term "part," "section," "portion," "member," or "element" when used in the singular can have the dual meaning of a single part or a plurality of parts. Finally, terms of degree such as "substantially," "about," and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A density detection device, comprising:
    a casing including an internal space to allow liquid to pass therethrough;
    an inflow path, the liquid passing therethrough, the inflow path being communicated with the internal space through an inlet, the inlet facing the internal space;
    an outflow path, the liquid passing therethrough, the outflow path being communicated with the internal space through an outlet, the outlet facing the internal space;
    a base being provided in the internal space to block the liquid flowing from the inlet, the base having a top side positioned above the inlet;
    a movable member having a bottom side opposed to the top side of the base, the movable member being configured to move to cause the bottom side to move toward and away from the top side of the base; and
    a density detection section being configured to detect density of a liquid layer formed between the bottom side of the movable member and the top side of the base while the bottom side of the movable member is closely positioned a predetermined distance relative to the top side of the base.

2. The density detection device according to claim 1, wherein a flow path is provided around the base to connect the inlet and the outlet.

3. The density detection device according to claim 1, wherein a groove is formed on the top side of the base, the groove being arranged along a flow direction of the liquid flowing into the internal space from the inlet.

4. The density detection device according to claim 1, further comprising a spacer that maintains the predetermined distance between the bottom side of the movable member and the top side of the base, the spacer making contact with the bottom side of the movable member and the top side of the base.

5. The density detection device according to claim 4, wherein the casing includes a fixation section provided around the base to fix the spacer while the spacer makes contact with the top side of the base.

6. The density detection device according to claim 5, wherein
the fixation section includes a first fixation part and a second fixation part, the first and second fixation parts being arranged such that the base is interposed therebetween, and
the top side of the base, and the bottom sides of the first and second fixation parts are positioned at the same height.

7. The density detection device according to claim 4, wherein the spacer has a through-hole extending toward the inlet and the outlet from the base.

8. An image forming apparatus, comprising:
an image forming section being configured to form an image on a medium with liquid developer including toner and liquid carrier; and
the density detection device being configured to detect a density of the liquid developer according to claim 1.

9. A density detection device, comprising:
a casing including an internal space being configured to receive an inflow of liquid;
a first liquid layer formation surface being provided in the internal space;
a movable member including a second liquid layer formation surface opposed to the first liquid layer formation surface, the movable member being configured to move to cause the second liquid layer formation surface to move toward and away from the first liquid layer formation surface;
a retainer retaining the movable member while the movable member moves freely;
a spacer maintaining a predetermined distance between the first and second liquid layer formation surfaces when the spacer makes contact with the first and second liquid layer formation surfaces; and
a density detection section detecting a density of a liquid layer formed between the first and second liquid layer formation surfaces while the second liquid layer formation surface is positioned a predetermined distance from the first liquid layer formation surface.

10. The density detection device according to claim 9, further comprising an urging member that urges the movable member toward the spacer while the second liquid layer formation surface makes contact with the spacer.

11. The density detection device according to claim 10, wherein
the retainer includes an interlocking member and a support member, the interlocking member is urged toward the spacer by the urging member, the interlocking member is interlocked with the movable member, and the interlocking member is configured to transmit the urging force of the urging member to the movable member,
the support member is configured to move to a first position and a second position, the first position causes the support member to support the interlocking member against the urging force of the urging member while the second liquid layer formation surface does not make contact with the spacer to prevent the urging force of the urging member from being transmitted to the movable member, the second position causes the support member to release support of the interlocking member while the second liquid layer formation surface makes contact with the spacer to allow the urging force of the urging member to be transmitted to the movable member, and
the movable member includes an interlocked part to allow the interlocking member to interlock therewith and clearance is produced between the interlocking member and the interlocked part to allow the movable member to move freely.

12. An image forming apparatus, comprising:
an image forming section being configured to form an image on a medium with liquid developer including toner and liquid carrier; and
a density detection device being configured to detect density of the liquid developer according to claim 9.

13. A density detection device, comprising:
a casing including an internal space and an opening, the internal space being configured to receive an inflow of liquid, the opening being formed above the internal space, the opening being communicated with the internal space;
a first liquid layer formation surface being provided in the internal space;
a movable member including a second liquid layer formation surface opposed to the first liquid layer formation surface above the first liquid layer formation surface, the movable member being configured to move to cause the second liquid layer formation surface to move toward and away from the first liquid layer formation surface;
a density detection section being configured to detect a density of a liquid layer formed between the first and second liquid layer formation surfaces while the second liquid layer formation surface is positioned a predetermined distance from the first liquid layer formation surface; and
a sealing member sealing the opening of the casing with the movable member, the sealing member including a through-hole to receive insertion of the movable member, the through-hole having a brim restricting horizontal movement of the movable member.

14. The density detection device according to claim 13, further comprising a restriction member that restricts horizontal movement of the movable member, the restriction member being provided below the sealing member in the internal space.

15. The density detection device according to claim 14, wherein the restriction member includes a plurality of pin members, the pin members being arranged to protrude toward the movable member from a lateral side of the movable member while the second liquid layer formation surface is positioned the predetermined distance from the first liquid layer formation surface.

16. An image forming apparatus, comprising:
an image forming section being configured to form an image on a medium with liquid developer including toner and liquid carrier; and
a density detection device being configured to detect density of the liquid developer according to claim 13.

* * * * *